(12) United States Patent
Crunkilton et al.

(10) Patent No.: US 8,142,200 B2
(45) Date of Patent: Mar. 27, 2012

(54) SLIP RING SPACER AND METHOD FOR ITS USE

(75) Inventors: Jeffrey Robert Crunkilton, Everett, WA (US); Craig Robert Bockenstedt, Kenmore, WA (US)

(73) Assignee: Liposonix, Inc., Bothell, WA (US)

( * ) Notice: Subject to any disclaimer, the term of this patent is extended or adjusted under 35 U.S.C. 154(b) by 542 days.

(21) Appl. No.: 12/051,081

(22) Filed: Mar. 19, 2008

(65) Prior Publication Data

US 2008/0243003 A1  Oct. 2, 2008

Related U.S. Application Data

(60) Provisional application No. 60/908,074, filed on Mar. 26, 2007, provisional application No. 60/976,867, filed on Oct. 2, 2007.

(51) Int. Cl.
*H01R 39/00* (2006.01)
(52) U.S. Cl. ....................................................... 439/21
(58) Field of Classification Search .................. 439/21, 439/20, 22, 27.11, 17, 272; 310/220, 221
See application file for complete search history.

(56) References Cited

U.S. PATENT DOCUMENTS

| | | | |
|---|---|---|---|
| 3,016,612 A * | 1/1962 | Lynott | ............................ 33/32.1 |
| 4,002,221 A | 1/1977 | Buchalter | |
| 4,059,098 A | 11/1977 | Murdock | |
| 4,211,949 A | 7/1980 | Brisken et al. | |
| 4,291,578 A | 9/1981 | Hetz et al. | |
| 4,326,418 A | 4/1982 | Pell, Jr. | |
| 4,368,410 A | 1/1983 | Hance et al. | |
| 4,437,033 A | 3/1984 | Diepers | |
| 4,459,854 A | 7/1984 | Richardson et al. | |
| 4,501,557 A | 2/1985 | Tamura et al. | |
| 4,556,066 A | 12/1985 | Semrow | |
| 4,567,895 A | 2/1986 | Putzke | |
| 4,593,699 A | 6/1986 | Poncy et al. | |

(Continued)

FOREIGN PATENT DOCUMENTS

GB  0 820 814  9/1959

(Continued)

OTHER PUBLICATIONS

International Search Report and Written Opinion of PCT Application No. PCT/US08/58156, dated Sep. 9, 2008, 10 pages total.

(Continued)

*Primary Examiner* — Tulsidas C Patel
*Assistant Examiner* — Harshad Patel
(74) *Attorney, Agent, or Firm* — Wood, Herron & Evans, LLP

(57) ABSTRACT

An interchangeable transducer for use with an ultrasound medical system having a keyless adaptor and capable of operating in a wet environment. The interchangeable transducer has an adaptor for engaging a medical system, an ultrasound transducer and additional electronics to provide a self-contained insert for easy replacement and usage in a variety of medical applications. A slip ring spacer is also disclosed, the slip ring spacer for use with a pancake slip ring having a base and flange configuration to form one or more channels around each contact ring of the pancake slip ring. The channels provide fluid isolation around each connector to help reduce electronic cross talk and contact corrosion between the connector pads of the slip ring while the slip ring is immersed in a wet environment.

7 Claims, 21 Drawing Sheets

U.S. PATENT DOCUMENTS

| | | | |
|---|---|---|---|
| 4,686,328 A * | 8/1987 | Ui et al. ............... 174/153 R |
| 4,865,042 A | 9/1989 | Umemura et al. |
| 4,874,326 A * | 10/1989 | Marolda, Jr. ............... 439/273 |
| 4,960,107 A | 10/1990 | Aida et al. |
| 5,076,276 A | 12/1991 | Sakurai et al. |
| 5,125,827 A | 6/1992 | Gellert |
| 5,143,063 A | 9/1992 | Fellner |
| 5,151,085 A | 9/1992 | Sakurai et al. |
| 5,163,433 A | 11/1992 | Kagawa et al. |
| 5,219,401 A | 6/1993 | Cathignol et al. |
| 5,259,383 A | 11/1993 | Holstein et al. |
| 5,291,090 A | 3/1994 | Dias |
| 5,301,660 A | 4/1994 | Rattner |
| 5,352,301 A | 10/1994 | Panchanathan et al. |
| 5,382,286 A | 1/1995 | Fanning et al. |
| 5,391,144 A | 2/1995 | Sakurai et al. |
| 5,412,180 A * | 5/1995 | Coombs, III ............... 219/385 |
| 5,419,327 A | 5/1995 | Rohwedder et al. |
| 5,419,761 A | 5/1995 | Narayanan et al. |
| 5,434,208 A | 7/1995 | Batelaan et al. |
| 5,476,438 A | 12/1995 | Edrich et al. |
| 5,477,736 A | 12/1995 | Lorraine |
| 5,498,164 A * | 3/1996 | Ward et al. ............... 439/15 |
| 5,505,206 A | 4/1996 | Walloch |
| 5,526,815 A | 6/1996 | Granz et al. |
| 5,568,810 A | 10/1996 | Hamers et al. |
| 5,575,664 A * | 11/1996 | Sobhani ............... 439/17 |
| 5,618,275 A | 4/1997 | Bock |
| 5,623,928 A | 4/1997 | Wright et al. |
| 5,626,486 A * | 5/1997 | Shelly et al. ............... 439/281 |
| 5,626,554 A | 5/1997 | Ryaby et al. |
| 5,669,150 A | 9/1997 | Guertin et al. |
| 5,676,159 A | 10/1997 | Navis |
| 5,687,717 A | 11/1997 | Halpern et al. |
| 5,688,235 A | 11/1997 | Sakurai et al. |
| 5,704,792 A * | 1/1998 | Sobhani ............... 439/21 |
| 5,738,098 A | 4/1998 | Brock-Fisher et al. |
| 5,738,635 A | 4/1998 | Chapelon et al. |
| 5,755,753 A | 5/1998 | Knowlton |
| 5,769,790 A | 6/1998 | Watkins et al. |
| 5,775,920 A * | 7/1998 | Henderson ............... 439/15 |
| 5,820,623 A | 10/1998 | Ng |
| 5,827,204 A | 10/1998 | Grandia et al. |
| 5,836,897 A | 11/1998 | Sakurai et al. |
| 5,840,572 A | 11/1998 | Copeland et al. |
| 5,851,120 A * | 12/1998 | Sobhani ............... 439/17 |
| 5,851,188 A | 12/1998 | Bullard et al. |
| 5,871,446 A | 2/1999 | Wilk |
| 5,928,169 A | 7/1999 | Schatzle et al. |
| 5,928,194 A | 7/1999 | Maget |
| 5,931,836 A | 8/1999 | Hatta et al. |
| 5,938,608 A | 8/1999 | Bieger et al. |
| 5,938,922 A | 8/1999 | Fulk, Jr. et al. |
| 6,019,775 A | 2/2000 | Sakurai et al. |
| 6,039,048 A | 3/2000 | Sillberg |
| 6,039,689 A | 3/2000 | Lizzi |
| 6,039,694 A | 3/2000 | Larson et al. |
| 6,056,735 A | 5/2000 | Okada et al. |
| 6,063,035 A | 5/2000 | Sakamoto et al. |
| 6,071,239 A | 6/2000 | Cribbs et al. |
| 6,085,749 A | 7/2000 | Wardle et al. |
| 6,113,558 A | 9/2000 | Rosenschein et al. |
| 6,132,219 A * | 10/2000 | Sobhani et al. ............... 439/17 |
| 6,142,748 A | 11/2000 | Harris et al. |
| 6,152,137 A | 11/2000 | Schwartz et al. |
| 6,217,515 B1 | 4/2001 | Yamakawa et al. |
| 6,233,476 B1 | 5/2001 | Strommer et al. |
| 6,241,753 B1 | 6/2001 | Knowlton |
| 6,261,249 B1 | 7/2001 | Talish et al. |
| 6,264,605 B1 | 7/2001 | Scirica et al. |
| 6,266,551 B1 | 7/2001 | Osadchy |
| 6,302,848 B1 | 10/2001 | Larson et al. |
| 6,306,146 B1 | 10/2001 | Dinkler |
| 6,309,355 B1 | 10/2001 | Cain et al. |
| 6,340,352 B1 | 1/2002 | Okada et al. |
| 6,350,245 B1 | 2/2002 | Cimino |
| 6,366,831 B1 | 4/2002 | Raab |
| 6,387,380 B1 | 5/2002 | Knowlton |
| 6,419,648 B1 | 7/2002 | Vitek et al. |
| 6,423,077 B2 | 7/2002 | Carol et al. |
| 6,425,867 B1 | 7/2002 | Vaezy et al. |
| 6,488,639 B1 | 12/2002 | Ribault et al. |
| 6,506,171 B1 | 1/2003 | Vitek et al. |
| 6,554,826 B1 | 4/2003 | Deardorff |
| 6,561,389 B1 | 5/2003 | Earle |
| 6,575,906 B1 | 6/2003 | Schembri, Jr. et al. |
| 6,607,498 B2 | 8/2003 | Eshel |
| 6,613,004 B1 | 9/2003 | Vitek et al. |
| 6,618,620 B1 | 9/2003 | Freundlich et al. |
| 6,623,423 B2 | 9/2003 | Sakurai et al. |
| 6,660,002 B1 | 12/2003 | Edwards et al. |
| 6,663,395 B2 * | 12/2003 | Sobhani ............... 439/21 |
| 6,679,875 B2 | 1/2004 | Honda et al. |
| 6,761,698 B2 | 7/2004 | Shibata et al. |
| 6,775,388 B1 | 8/2004 | Pompei |
| 6,884,083 B2 * | 4/2005 | Shepherd ............... 439/18 |
| 6,921,269 B2 * | 7/2005 | Johnson et al. ............... 439/13 |
| 6,962,498 B2 * | 11/2005 | Kohen ............... 439/21 |
| 7,011,520 B2 | 3/2006 | Rahman et al. |
| 7,063,692 B2 | 6/2006 | Sakurai et al. |
| 7,255,678 B2 | 8/2007 | Mehi et al. |
| 7,273,459 B2 | 9/2007 | Desilets et al. |
| 7,387,530 B2 * | 6/2008 | Shinohira et al. ............... 439/519 |
| 7,435,112 B1 * | 10/2008 | Miller et al. ............... 439/141 |
| 7,462,066 B2 * | 12/2008 | Kohen ............... 439/537 |
| 7,771,202 B2 * | 8/2010 | Amotz et al. ............... 439/39 |
| 7,802,995 B2 * | 9/2010 | Lai ............... 439/66 |
| 7,811,091 B2 * | 10/2010 | Koyama ............... 439/17 |
| 2002/0043499 A1 | 4/2002 | Hammen et al. |
| 2002/0082528 A1 | 6/2002 | Friedman et al. |
| 2002/0107538 A1 | 8/2002 | Shibata et al. |
| 2002/0128592 A1 | 9/2002 | Eshel |
| 2003/0004439 A1 | 1/2003 | Pant et al. |
| 2003/0073325 A1 * | 4/2003 | Canizales, Jr. ............... 439/17 |
| 2003/0076591 A1 | 4/2003 | Ohmori et al. |
| 2003/0083536 A1 | 5/2003 | Eshel et al. |
| 2005/0016769 A1 | 1/2005 | Wallace |
| 2005/0027195 A1 | 2/2005 | Govari |
| 2005/0101945 A1 | 5/2005 | Sakurai et al. |
| 2005/0154314 A1 | 7/2005 | Quistgaard |
| 2005/0187495 A1 | 8/2005 | Quistgaard et al. |
| 2007/0035201 A1 | 2/2007 | Desilets et al. |
| 2007/0155200 A1 * | 7/2007 | Shinohira et al. ............... 439/76.2 |
| 2007/0167825 A1 | 7/2007 | Lee et al. |
| 2009/0240146 A1 * | 9/2009 | Bockenstedt et al. ............... 600/439 |
| 2010/0001533 A1 * | 1/2010 | Jefferson ............... 290/55 |
| 2010/0279539 A1 * | 11/2010 | Lo et al. ............... 439/426 |

FOREIGN PATENT DOCUMENTS

| WO | WO 93/01752 | 2/1993 |
| WO | WO 00/36982 | 6/2000 |
| WO | WO 02/054018 A2 | 7/2002 |

OTHER PUBLICATIONS

Ayme et al., Occurance of transient cavitation in pulsed swatooth ultrasonic fields *J. Acoust. Soc. Am.* (1988) 84(5):1598-1605.

Clarke et al., Physical and chemical aspects of ultrasonic disruption of cells *J. Acoust. Soc. Am.* (1970) 47(2):649-653.

Flynn et al., A mechanism for the generation of cavitation maxima by pulsed ultrasound *J. Acoust. Soc. Am.* (1984) 76(2):505-512.

Fry et al., Threshold ultrasonic dosages for structural changes in the mammalian brain *J. Acoust. Soc. Am.* (1970) 48(6):1413-1417.

Kinney, Body contouring with external ultrasound *Plastic & Reconstruct. Surg.* (1999) 103:728-729.

Lele, Thresholds and mechanisms of ultrasonic damage to 'organized' animal tissues *Symposium on Biological Effects and Characterizations of Ultrasound Sources* (1977) Hazzard et al., Eds., pp. 224-239.

USPTO, Office Action issued in related U.S. Appl. No. 12/051,073 dated Sep. 6, 2011.

USPTO, Office Action issued in related U.S. Appl. No. 12/051,073 dated Apr. 12, 2011.

\* cited by examiner

SLIP RING SPACER AND METHOD FOR ITS USE

CROSS-REFERENCES TO RELATED APPLICATIONS

The present application claims the benefit of provisional U.S. Application Nos. 60/976,867, filed Oct. 2, 2007 and 60/908,074 filed on Mar. 26, 2007, the full disclosures of which are incorporated herein by reference.

This application is related to, and claims partial priority from, Provisional U.S. Patent Application No. 60/908,074, entitled "Interchangeable High Intensity Focused Ultrasound Transducer" filed on Mar. 6, 2007. This application is also related to U.S. patent application Ser. No. 11/027,912 entitled "Ultrasound Therapy Head with Movement Control" filed on Dec. 29, 2004 and U.S. patent application Ser. No. 11/027,919, entitled "Component Ultrasound Transducer," also filed on Dec. 29, 2004. All identified applications are herein incorporated by reference in their entirety.

BACKGROUND OF THE INVENTION

The present invention relates to a sealing adaptor for use with a interchangeable transducer for use within a wet environment transducer housing.

Some high intensity focused ultrasound (HIFU) transducers have limited life span because of the high power levels that may tax their physical construction. These transducers degrade and fail for a variety of reasons much faster than transducers used in other medical fields (like diagnostic ultrasound, or other low power applications). Transducers designed for therapeutic ultrasound applications delivering therapeutic power levels may suffer de-lamination of their metallization layers, pitting or physical destruction of the transducer caused by cavitation or thermal effects from exposure to very high temperatures.

To combat some of these side effects of HIFU operation, system designs may use HIFU transducers below the threshold where damage may occur to the transducer itself. Other systems use water baths with degassed circulating water, or design their therapy regimens with long intervals between therapy pulses. These extended pauses between pulses produce a low pulse repetition frequency (PRF) allowing the transducer to cool, and negative effects in tissue to dissipate.

Unfortunately, some therapy regimen require HIFU with a higher PRF, or continuous operation of the transducer for certain lengths of time that preclude low PRF operation. These higher PRF and/or continuous wave (CW) style regimen are desirable when the treatment is designed to maximize the amount of tissue destruction to be achieved in a certain period of time. In these types of operations, transducer degradation necessitates a frequent replacement of the HIFU transducer. Replacement is made difficult in that the transducers are generally expensive and delicate components, so handling the transducers is usually kept to a minimum. Further more, transducers in therapeutic medical systems are often imbedded into large bulk chambers filled with water, or attached in a manner that precludes easy removal and replacement of the transducer. The transducer environment may contain water, which should not be permitted to mix with the system electronics. The presence of water during a transducer exchange can make the replacing of a transducer messy and difficult. Once the transducer is replaced, water may linger between the electrical connectors between the system and the new transducer. System performance may be degraded due to electrode corrosion or signal cross-talk among the conduction paths caused by the presence of water or other fluids.

Thus it would be desirable to provide a transducer connector, or connecting means, that provides an easier method of removing and connecting transducers to a medical ultrasound device that is compatible with the demands of a wet environment, and capable of handling all system requirements without degradation in performance.

Thus it is an objective of the present invention to provide a connectorized transducer that can be connected to a therapy head or medical system with as few steps as practical, while preserving the environmental conditions of the connection.

Another objective is a connection that has a high reliability and ease of use, to promote a user friendly procedure for removing and/or installing transducers in the medical system.

Yet another objective is to provide a transducer that provides various features and operation parameters to expand or broaden the type of transducers a user may connect with the medical system.

Still another objective is a transducer that possesses the necessary driving electronics particular to their designed features, so as to reduce the required programming and electronics of the main system.

Still another objective is to provide a simple disposal path for used components.

Still another objective is a sealing device for electrical signal isolation or electrical connector isolation in a wet environment.

BRIEF SUMMARY OF THE INVENTION

These and other objectives are achieved through an interchangeable transducer adapted for use with a high intensity focused ultrasound (HIFU) medical system. The interchangeable transducer has a housing that is generally rigid and hollow. The housing has two open ends, one adapted for fitting a HIFU transducer, and the other end having an isolation layer and electrical connection for electrical signal and power communication with the HIFU medical system. The interchangeable transducer is adapted to fit into a socket style receptacle on the medical system. The transducer is ideally replaced by the user, so the portion of the transducer which fits into the socket is designed for easy insertion and extraction. Easy insertion is achieved through an orientation free, low engagement force connection between the transducer and the medical system which allows easy user access to the transducer.

A slip ring spacer is also described herein for use with a wet electrical connection having a pancake style slip ring. The slip ring spacer has a base formed from a non-conductive material. Multiple apertures extend through the base. The apertures are designed to sheath electrical connectors which extend through the base. There are one or more flanges extending from the base. The flanges are arranged so as to isolate the apertures into cells. Assemblies comprising a slip ring and the slip ring spacer provide wet seals and may be exposed to wet environments.

Additional embodiments and methods of making and using the interchangeable transducer are also herein described.

DETAILED DESCRIPTION OF THE INVENTION

Figure 1:
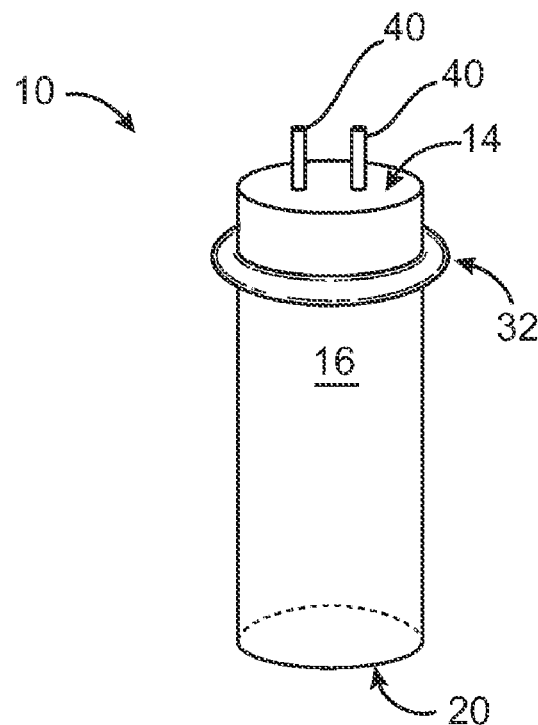
FIG. 1 shows an exterior view of an interchangeable transducer.

Described herein are various forms of replaceable transducers for use with high intensity focused ultrasound (HIFU) medical systems. The basic design of the interchangeable transducer incorporates a housing which is hollow and generally rigid. The housing holds within it a transducer, such as one compatible with HIFU medical systems, electrical pathways (electronics) for connecting the transducer to a medical system so the transducer can be properly controlled, and a connector that allows the interchangeable transducer to be removed and/or inserted into a receptacle on the medical system. The transducer housing has a shape and electrical connection assembly that allows the housing to be inserted in any radial orientation relative to the system receptacle axis. The axial symmetry may allow for two or more orientations, and desirably an unlimited number of orientations. For visualization purposes only, one may imagine the ease of inserting a mini-plug for headphones into a portable music player. The radial orientation of the plug to the receptacle does not matter, and during use if the plug is rotated within the socket, there is no interruption of the power and signal sent to the head phones. This concept is analogous to the type of adaptor and socket used in the interchangeable transducer connection described herein.

In the following paragraphs, various aspects and embodiments of the apparatus will be described. Specific details will be set forth in order to provide a thorough understanding of the described embodiments of the present invention. However, it will be apparent to those skilled in the art that the described embodiments may be practiced with only some or all of the described aspects, and with or without some of the specific details. In some instances, descriptions of well-known features may be omitted or simplified so as not to obscure the various aspects and embodiments of the present invention.

Parts of the description will be presented using terminology commonly employed by those skilled in the art to convey the substance of their work to others skilled in the art, including terms of operations performed by or components routinely used in ultrasound systems, medical ultrasound systems and HIFU systems. As well understood by those skilled in the art, the operations typically involve producing and controlling the wave form of the transducer through a transmitter signal which generally uses well understood electronics components and controllers. Signal control, depends primarily on the desired objective for using HIFU. Novel variations from prior art devices will be presented here in a straight forward and simple manner so as to highlight the elements necessary to practice the present invention, but not to be prolix in description for those details which are well understood in the art. The term system includes general purpose as well as special purpose arrangements of these components that are stand alone, adjunct or embedded.

Various operations may be described as multiple discrete steps performed in turn in a manner that is most helpful in understanding the present invention. However, the order of description should not be construed as to imply that these operations are necessarily performed in the order they are presented, or even order dependent.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment.

The present invention relates to an interchangeable transducer apparatus and methods of making the same, for use with medical ultrasound systems, particularly those considered HIFU medical systems.

The transducer described herein incorporates both novel physical components and design, combined with existing materials in a novel fashion to produce a transducer insert meeting one or more of the objectives of the invention. The combinations of various novel elements in one embodiment will meet some objectives, while a different combination of novel elements will meet different objectives. The collective whole of novel developments and arrangements of existing parts contributes to a design that satisfies the most objectives, though not necessarily all objectives in a single design. Different objective requirements will call for different combinations of the inventive concepts herein described.

The transducer insert may be suitable for any number of medical devices or medical systems desiring to use an easily replaceable transducer. In pending U.S. patent application Ser. No. 11/027,912 "Ultrasound Therapy Head with Movement Control," filed 29 Dec. 2004 (commonly assigned and herein incorporated by reference), a therapeutic ultrasound system is described having a therapy head. The therapy head contains a first chamber, being wet, in which a transducer is positioned. There is a second chamber, which may be wet or dry, that contains a motor drive system. The motor drive system uses one of several possible means to move the transducer in the first chamber. Means described include use of actuators that extend from the motor side chamber to the transducer side chamber, a slide positioned on the motor chamber with a magnetically connected transducer in the transducer chamber, or various mechanical translation components for converting the work produced from the motors into the movement of the transducer through a barrier between the two chambers.

The interchangeable transducer, (also referred to herein as a connectorized transducer or transducer insert), of the present design is well suited for use in a therapy head of the previous description. The interchangeable transducer or transducer insert is formed from a housing having an adaptor end and an acoustic end. There is a communication port at the adaptor end. The adaptor end is designed to fit into a corresponding receptacle on or in the medical ultrasound system. In one embodiment the transducer adaptor end has a plurality of orientations for removably engaging a receptacle in the medical ultrasound system. There is a transducer at the acoustic end, and a means for electrical communication between the communication port and the transducer.

The adaptor end may be a male or female type part, while the receptacle would be the logical corresponding type part. While we describe primarily a male adaptor and a female receptacle, it should be understood that the adaptor end of the transducer insert can be the female component while the system side receptacle is the male component. The adaptor end and corresponding receptacle end are designed in a manner to provide a plurality of working orientations in which the transducer insert can be placed into the system. In one embodiment the plurality of orientations may simply be a slotted design for the adaptor and receptacle. The electronics of the adaptor and receptacle are arranged in a manner as to allow a "key-less" type of connection. Regardless of which orientation the insert is placed into the receptacle, the insert will connect with the system and operate properly. The connection between the adaptor and receptacle may be any design having symmetry about an axis, so the insert may be rotated about the axis so the insert can be fit into the receptacle in at least two directions (normal and flipped). If the connection is shaped like a triangle, three orientations would be possible. For a square four orientations would be possible. This dynamic continues to the logical and most desirable shape of having a circular shaped adaptor where absolute radial freedom is afforded. The insert may be placed into the system receptacle at any radial orientation and proper electrical connection is guaranteed. Regular shapes are not required to make the adaptor connection. Irregular shapes may also be used so long as they are symmetrical. The symmetry of the connection provides the advantage to the user of not having to worry about the orientation of the transducer insert relative to the system socket (receptacle). So long as the shape of the connector matches the receptacle the user knows the orientation will work.

Electrical communication is required from the ultrasound medical system and the transducer within the transducer insert. Electrical communication enters the transducer insert at the communication side. Electrical communication means providing any combination of power, signal or ground connections from the transducer to the ultrasound system through the communication port in the transducer insert. This communication can be achieved using wires, cables, connector pins, or other electron conveying instruments as known in the art. In one embodiment, the connection may be wires running directly from the communication port to the transducer in a "dumb" design, where no on board intelligence is provided in the insert. In another embodiment, intelligence may be incorporated into the insert by adding electrical components to an electrical circuit used to provide electrical communication from the communication port to the transducer. A variety of components may be used in an intelligent design. Electrical components may include a tuning transformer for optimizing the transducer, sensors for measuring various parameters about the environment within the transducer insert, sensors for monitoring the transducers performance and/or safety, components for recording measured or detected data, IC chips for running programmed applications or storing information within the insert, or any other operation desired.

In another embodiment of the present invention, the electrical communication between the communication port and the transducer may be provided by a two stage spring pin connection scheme. A first stage set of connection pins connects the communication port to an electrical circuit board. The circuit board may be a PCB/PCBA and may further be a pancake slip ring style PCB/PCBA. A second stage set of connection pins connects the electrical circuit to the transducer. Electrical communication enters the communication port from the ultrasound system. The Electrical communication then travels to the electronic circuit. The circuit board may provide the proper coordination and layout of the various electrical components, and assures proper handling of Electrical communication between the system and the transducer. From the electrical circuit, Electrical communication continues to the transducer. Any return Electrical communication from the transducer may follow a similar route back from the transducer to the circuit board, and then back to the system.

The insert may have various data recorders, sensors or programmable components within it. These elements may be on the circuit board. Various possible components that may be incorporated into the insert include a chip for tracking the number of times the transducer has been used, sensors which determine the proper coupling between the transducer and the patient, sensors to determine if the transducer is properly installed into the ultrasound system, or sensors to determine the safe operation of the transducer while providing therapy output. There may also be a tuner for a second transducer such as an "A" line transducer for providing simple imaging information to the user or to the system.

The transducer insert may also be constructed to operate with a component style ultrasound system such as those described in U.S. patent application Ser. No. 11/027,919 entitled "COMPONENT ULTRASOUND SYSTEM" and filed on Dec. 29, 2004 (commonly assigned and herein incorporated by reference). In this embodiment, the insert has an adaptor for fitting to an ultrasound system having two or more identical sockets for receiving more than one type of insert, where one of the inserts may be a transducer insert as described herein. In a component ultrasound transducer, there are two or more sockets in the therapy head. The sockets are identical and the inserts used within the sockets may be plugged into any one of the sockets, Each insert has a challenge and recognition component programmed in it, so when the insert is plugged in, the ultrasound medical system can identify each individual insert and know how to properly use it. The system can handle multiple kinds of inserts simultaneously. Each insert may have a different focal depth, performance parameter or use requirement, the system can determine and properly handle the proper operation of all inserts. Desirably the transducer inserts would be properly utilized by the system automatically (without specialized user contribution or instruction to the system other than that used for a single receptacle ultrasound system using a transducer insert).

Use of modern materials and electronics greatly reduces the costs of manufacturing transducers for the medical ultrasound systems disclosed herein. This cost reduction and ease of manufacturing allows replacement parts to be disposable when worn out or no longer desired.

In addition to the transducer insert described herein, a novel structure is now disclosed allowing an electrical connection to be made in a wet environment. The novel structure is a slip ring seal, designed for use with a pancake style slip ring PCB. The slip ring seal has a base, two or more apertures extending through the base, and flanges extending from the base to isolated the apertures into cells. The flanges may define cells discretely formed around each aperture, or around a select group of apertures, or a combination of the two.

The connection between the transducer insert and the system is generally a wet environment. Particularly during operation of the transducer the chamber in which the transducer is located is fluid filled. Various fluids are suitable for use in the transducer chamber where the transducer of the present description can be used, in general water is the most common fluid used due to ease of availability, cost and performance characteristics. Reference herein to fluids or water should be understood to incorporate which ever fluid is most suitable for the intended use and design of the transducer, since not all operations will prefer water when another compatible fluid may be superior for the particular application.

Now turning to the accompanying drawings, it should be understood the drawing figures are provided to enhance the description provided. Elements shown in the figures are not necessarily illustrated to scale with respect to other drawings, or other parts within the same drawing. The parts or figures should not be taken in any absolute sense of actual design elements other than as illustrations of embodiments for the purpose of understanding the disclosure herein.

A simplified exterior view of the interchangeable transducer 10 is shown in FIG. 1. The transducer 10 has a housing 16 represented as generally cylindrical. The housing 16 is desirably rigid and hollow. The housing 16 has a transducer end 20, and an electrical connector and sealed end 14. External electrical connectors 40 extend through the seal end 14 and are designed to connect to the appropriate electrical lines from the medical system. These may include a transmit/receiver line, ground and power. Additional lines may be provided depending on the need or application of the medical system. The interchangeable transducer need only have addition electrical connectors and support circuitry to enable those capabilities. An adaptor 32 is also provided to allow physical engagement of the transducer 10 to a HIFU medical system.

Figure 2:
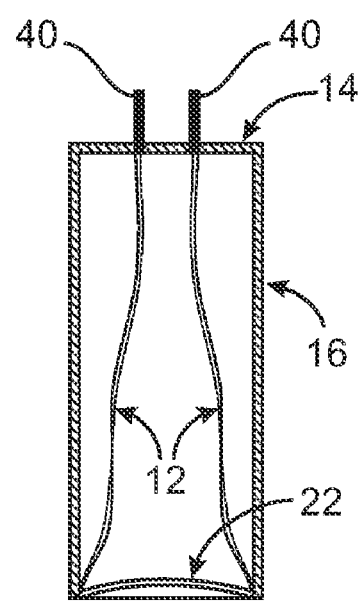
FIG. 2 is a cut away view of an interchangeable transducer.

A simplified interior view of the interchangeable transducer 10 is now illustrated (FIG. 2). Once again the seal end 14 has external electrical connectors 40 for electrical connection to a medical system. The external electrical connectors 40 may extend through the seal end 14 to connect to a component within the housing 16, or there may be an intermediate connection through the seal end from the interior of the housing. Desirably the external connectors extend through the seal end to provide electrical contact between the socket of the medical system, and the interior of the interchangeable transducer. The transducer 22 is shown at the bottom or lower section of the housing 16. The transducer 22 is electrically connected to the connectors 40 by wires 12. Electrical signals from the ultrasound system to the transducer 22 (or visa-versa) may include power, ground, transmit, receive, data or other signals and information as desired. The housing may also contain one or more electrical components as part of the transducer's control circuit.

Figure 3:
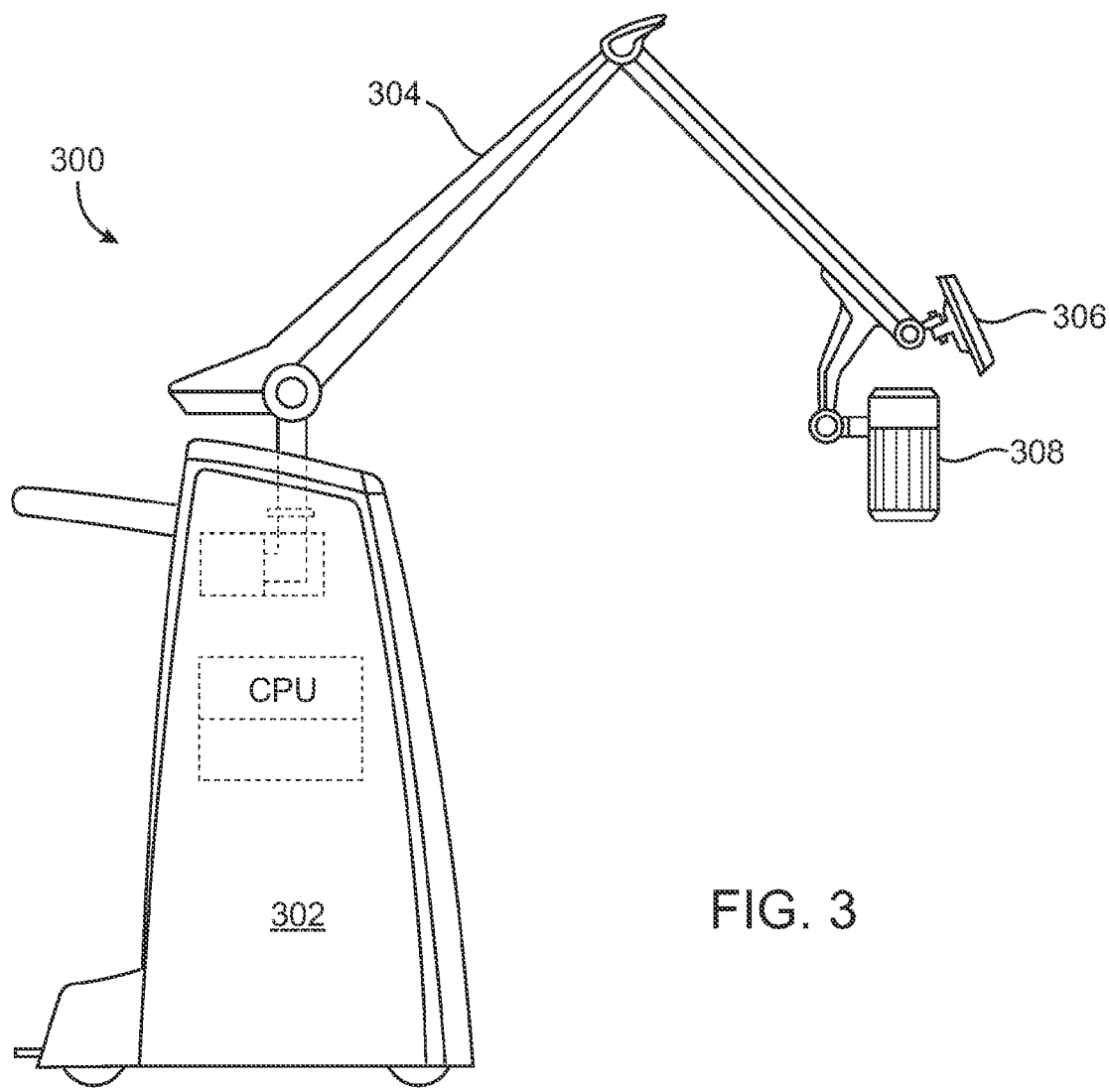
FIG. 3 shows a system for use with an interchangeable transducer.

The interchangeable transducer 10 has a connector or other adapter allowing it to engage into a receptor on a medical device system (FIG. 3). A medical system 300 that might use an interchangeable transducer as described herein, is shown having base 302, an articulating arm 304, with a display screen 306 and a therapy head 308. Within the therapy head 308, there is an adaptor for receiving an interchangeable transducer. A computer or other electronic intelligence (CPU) is also provided to operate the system 300 and the transducer 10.

The internal components of the therapy head 308 are generally described along with the method of changing out transducers (FIGS. 4A-4E).

Figure 4A:
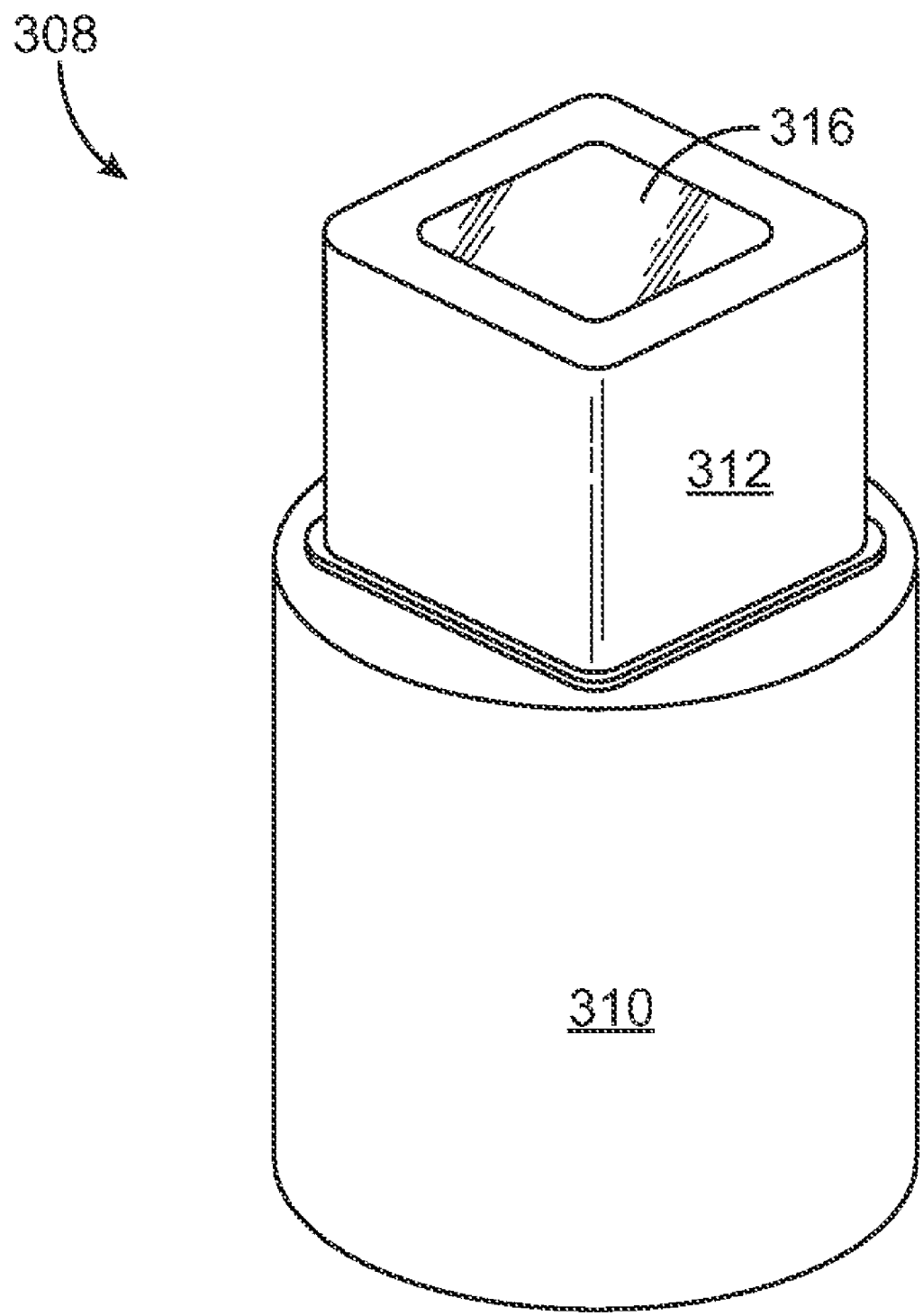
FIGS. 4A-4E illustrate a method of swapping a transducer.
Figure 4B:
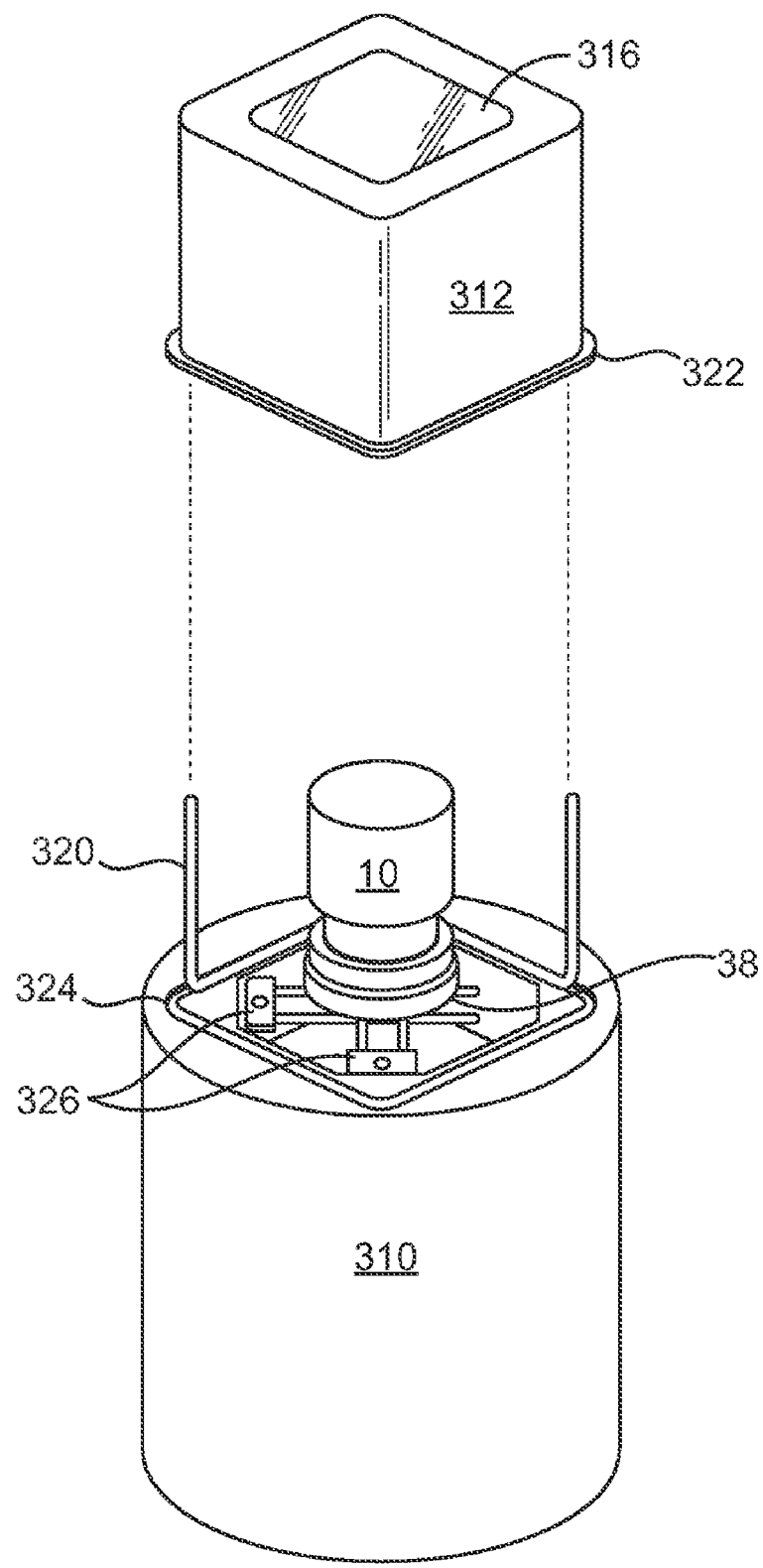

Any water or other fluids in the therapy head 308 are desirably drained from the therapy head so that water does not splash out of the therapy head when opened. Having water or other fluids in the therapy head is not an impediment to the removal and installation of transducers described herein, so it is not necessary to completely drain the therapy head. In one embodiment the therapy head 308 is inverted, so the main transducer chamber 310 is positioned on the bottom. The therapy head 308 has a removable cap 312 section, with a transmission window 316 (FIG. 4A).

The cap 312 is removed (FIG. 4B) exposing the interior of the therapy head transducer chamber 310. The interchangeable transducer 10 is connected to a receptor socket 38. A pair of water lines 320 are used to circulate water inside the transducer chamber when the cap 312 is sealed to the transducer housing 310. There are mating flanges 322 on the treatment cap 312 and bulkhead 324 that contain an O ring seal on the transducer housing 310 that when assembled create the water tight seal of the chamber (not shown). Under the receptor 38, the transducer chamber may have motors or motor cams 326 or drive shafts connected to a mechanical drive system for moving the receptor 38.

Figure 4C:
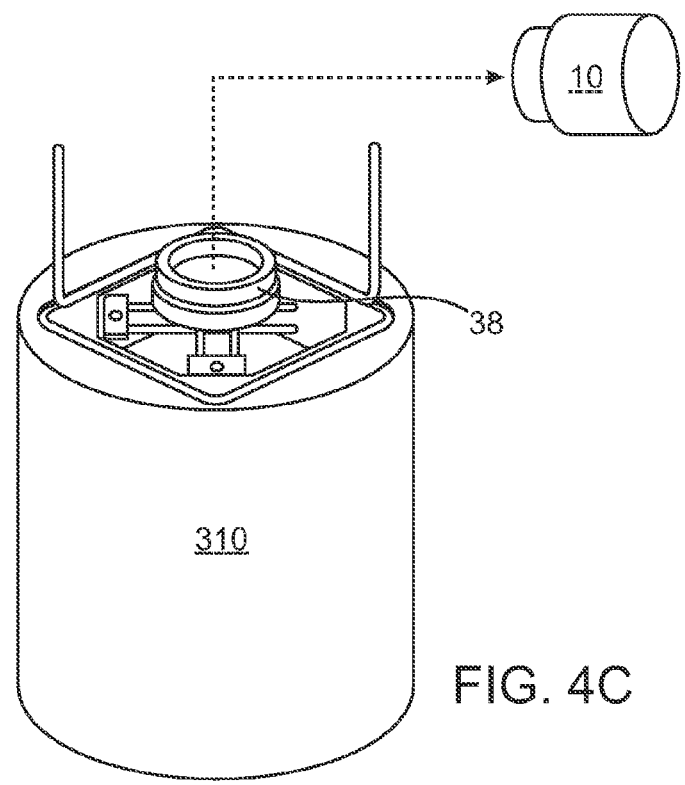

Once the cap 312 is removed, the interchangeable transducer 10 can be removed (FIG. 4C). Desirably the transducer can be lifted straight out of the receptor 38, or detached from the receptor with a minimal amount of force (like twisting or rocking). The empty receptor 38 has a PCB slip ring which may get wet during this step, and the presence of water on the PCB is of no concern.

Figure 4D:
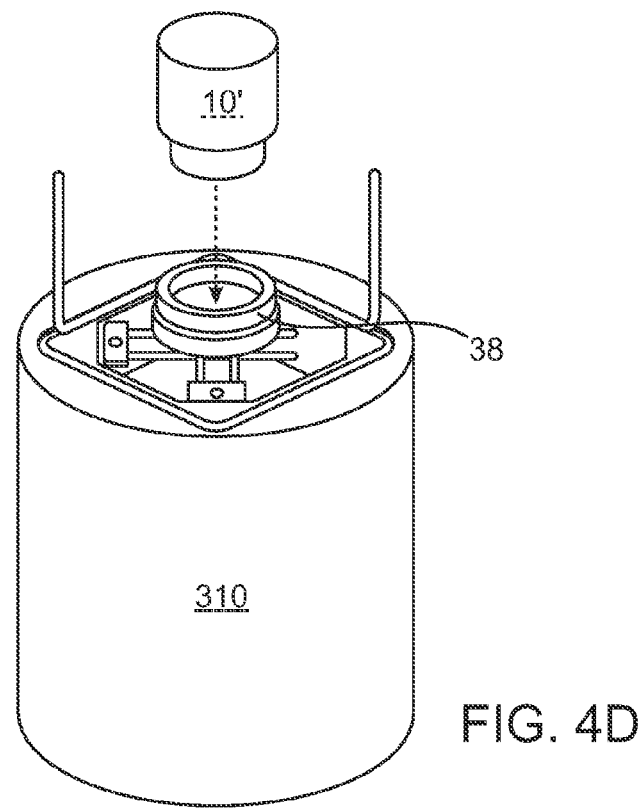
Figure 4E:
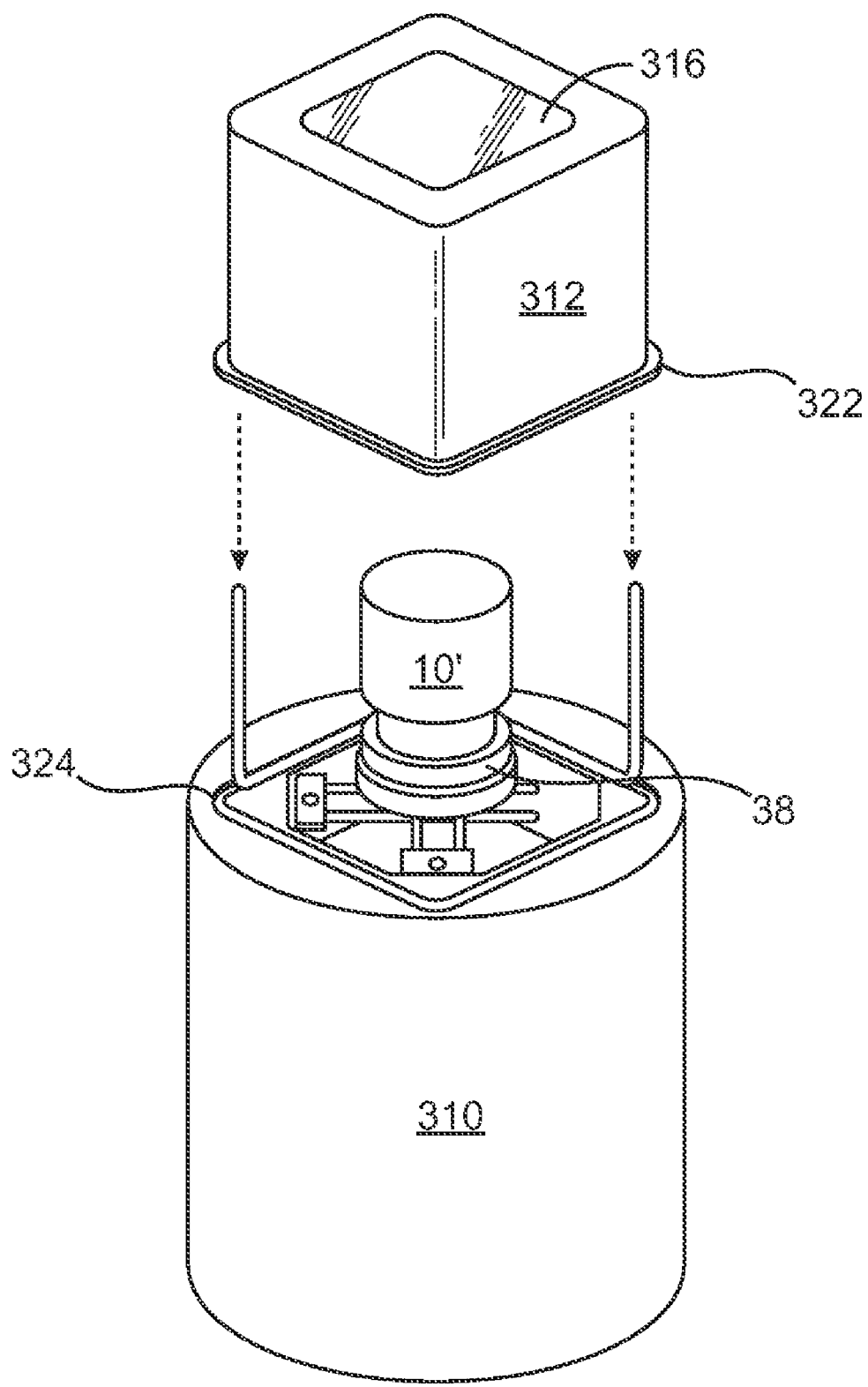

A new transducer 10' is now seated onto the receptor 38 in place of the old transducer 10 (FIG. 4D). Again the insertion force for placing the new transducer 10' is desirably fairly low, allowing any user to insert the new transducer 10' easily and quickly. The round shape of the transducer plug and the receptor 38 allow for any radial orientation when the new transducer 10' is seated into the receptor 38. The cap 312 is then repositioned over the transducer chamber 310 to re-form the therapy head 308 (FIG. 4E).

Once the new transducer is in place, it may be desirable to refill the water chamber, activate the medical system 300, and allow the system to communicate with the new transducer 10' to ensure the transducer is properly seated in the receptor 38, and that the transducer is responding normally. The system may use a 'challenge and answer' protocol to determine the nature of the transducer, and establish the appropriate therapy regimen to use with the particular transducer. The transducer 10 may have an integrated circuit (IC) 30 on board that can provide detailed information to the medical system once it is properly connected. Alternatively the IC may be used for other purposes (see below).

A connector or adaptor 32 is shown on the outside of the housing 16 (FIG. 1). The connector 32 allows the transducer housing 16 to mate with a socket or receptacle 38 of a medical system 300. The connector 32 desirably allows the housing 16 to be inserted into the socket or receptacle with a low insertion force to provide easy insertion or removal. The electrical connectors 40 are designed to operate in conjunction with the mechanism used to mate the transducer 10 to the receptor 38, so the electrical connectors 40 can establish and maintain contact with the appropriate system side electronic channels regardless of the radial orientation of the transducer when mated to the receptor. The connector 32 similarly can engage the socket 38 in any radial orientation. The receptor or socket 38 has a receiving element 36 for the connector 32. The connector 32 for engaging the socket may be mechanical, magnetic or electromagnetic in nature. As long as the connector can hold the transducer housing in its proper place in the socket and allow for any radial orientation for insertion and removal, the connector will be sufficient for the intended use.

Figure 5A:
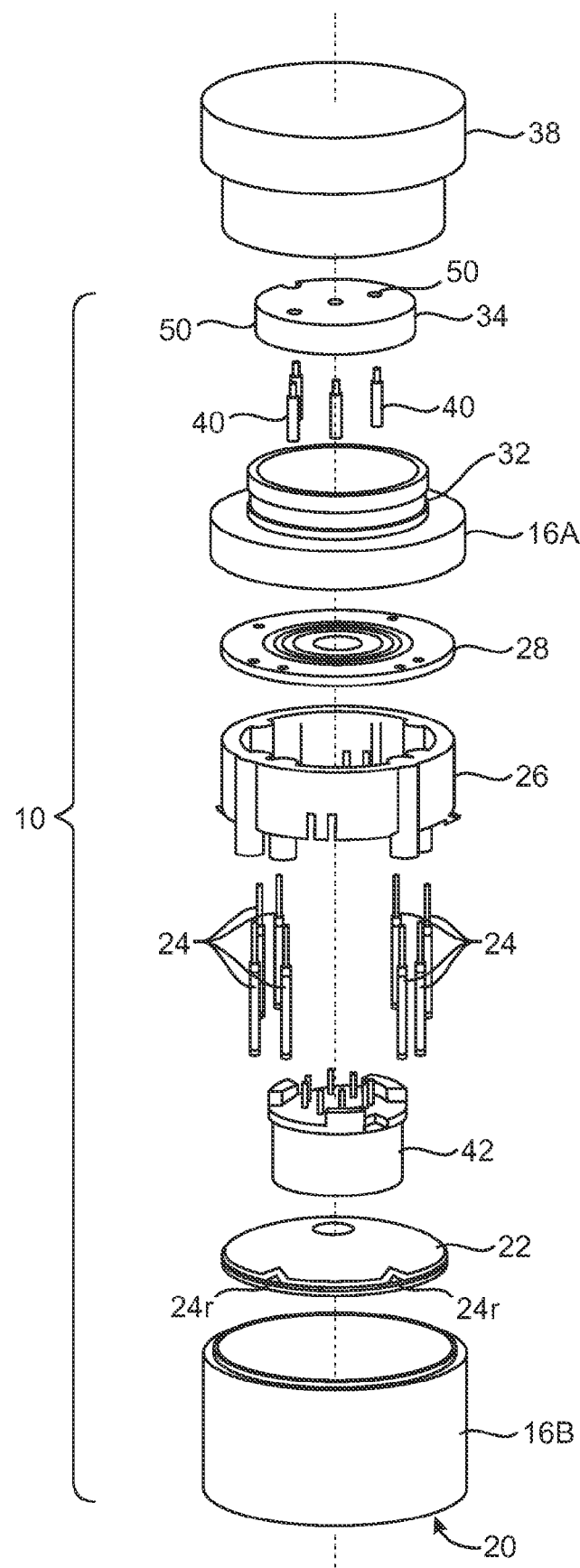
FIG. 5A shows an exploded view of one embodiment of the interchangeable transducer.

The interchangeable transducer assembly is now described (FIG. 5A). In this embodiment, the housing 16 is made from two sections, a lower portion 16B for receiving the transducer 22, and an upper portion 16A adapted for connection with the medical system socket 38. The transducer 22 is shown having a set of pin receptors 24r where the electrical pins 24 attach to the transducer. The electrical pins 24 extend from the interface 28 to the transducer and pass through the concentric liner 26. Desirably the liner has apertures for lining up the connection points on the interface and the transducer. An optional transformer 42 can be connected to the interface 28, and would sit within the aperture defined by the concentric liner 26.

The lower portion 16B may be assembled by first inserting the transducer 22 into the lower portion 16B. The transducer 22 may be secured using epoxy or resin along the transducer rim to seal the transducer to the aperture defined by the housing opening 20. The electrical connector pins 24 are inserted into the concentric liner 26, and then the connector pins 24 are oriented to match the transducer receiver placements 24r. The concentric liner 26 is then placed into the lower portion and secured. Electrical components such as the transformer 42, or the data IC (not shown) may be attached to the PCB 28, and then the PCB 28 is lined up to match the desired connector pin 24 layout. The PCB 28 has predefined lands on both its upper and lower surface. These lands correspond to the pin orientation for the electrical connector pins 24 of the lower portion, and for the electrical pins of the upper portion 40.

The upper portion 16A is similarly assembled. The upper portion is sealed across the top, and the electrical pins 40 that extend through the top of the upper portion 16A are sealed against fluid flow from the outside of the housing to the inside. The electrical pins 40 may be soldered in place, or fixed with an epoxy or other agent to provide the fluid seal between the upper portion 16A and the apertures needed for the pins. The upper connector pins 40 are inserted through the isolation layer 34 in a predefined arrangement matching the upper lands of the PCB 28. The connector pins may be any type of electrical pins suitable for use in an interchangeable design. Spring pins, pogo-pins, spring clips and other tensioned electrical connectors are desirable in one embodiment due to their expansive nature. Spring loaded connectors allow a greater margin of safety in physical distance between the transducer and PCB. Once the connection pins 40 are in place, the isolation layer 34 is lowered into the upper housing 16A. The isolation layer 34 is desirably attached to the upper portion so that the upper housing 16A and isolation layer 34 can be moved as a single unit. The isolation layer 34 may be attached using an adhesive compound between the isolation layer and the top of the upper housing. Alternatively the isolation layer 34 may be constructed so there is an interference fit between the isolation layer and the upper section of the housing. Desirably the adhesive or interference fit would prevent water from pooling underneath the isolation layer and the housing. The upper housing is then lowered onto the lower housing assembly so the connector pins 40 match the PCB land layout (FIG. 5A). The entire transducer housing may be filled with an inert gas to promote stability and operational life span of the internal components.

Figure 5B:
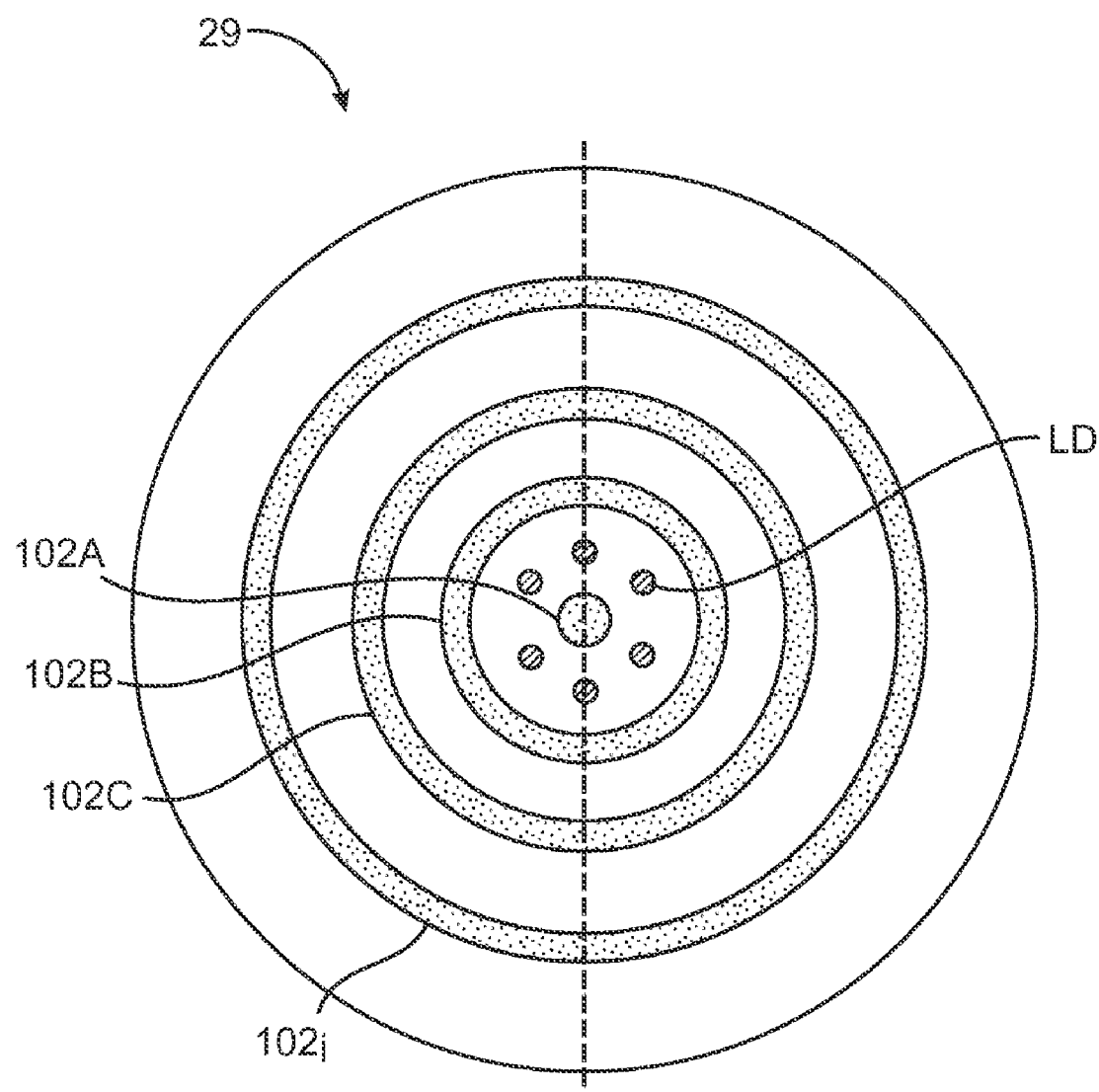
FIG. 5B provides an alternative embodiment of a PCB for use inside the insert.

In an alternative embodiment, the transducer insert 10 replaces the standard PCB 28 with a slip ring PCB 29 (FIG. 5B). In this embodiment there are discrete lands LD or traces for direct attachment to particular components (transformer, IC chips, etc. . . . ) as well as traces made into slip rings 102a-i for connection to various connectors. In this embodiment the transducer insert realizes an advantage in assembly by having electrical communication with portions of the transducer insert not directly attached to the PCB 29 in that those non attached components are free from discrete orientation relative to the PCB 29. Parts desirably directly connected to the PCB 29 would connect to discrete lands sites LD, while pin connections 24, 40 could connect to the land rings. The transducer 22 may also have a land ring instead of discrete connection points 24r. By utilizing land rings in the various components within the transducer, freedom from particular orientations are achieved, and thus provide advantages in manufacturing/assembly of the parts and sub components.

Although the medical system socket 38 is illustrated (FIG. 5A), this component is not a part of the interchangeable transducer 10, and is merely illustrated here to show the alignment of all the parts described. Desirably the socket utilizes a pancake style slip ring to improve contact regardless or radial orientation.

The transducer used in the interchangeable transducer design may have a single fixed zone, or be designed having two or more focal zones. The transducer may have an imperfect focal zone achieved through a mechanical distortion formed in the transducer, such as those described in U.S. patent application Ser. No. 10/816,197 entitled "VORTEX TRANSDUCER" and filed on Mar. 31, 2004, and U.S. patent application Ser. No. 11/439,706 entitled "Medical Ultrasound Transducer Having Non-Ideal Focal Region" filed May 23, 2006. (both applications commonly assigned and herein incorporated by reference). The vortex transducer and the non-ideal focal region transducers allow for a focal region in a circular or donut shaped pattern wherein the pattern is produced by a mechanical offset in the bowl of the transducer. The isolation layer 34 is primarily used to prevent electrical cross talk and contact corrosion among and between the electrical contacts 40. The shape and size of the focal region can be mathematically calculated and an appropriate mechanical shape to a transducer can be manufactured. This allows the transducer to focus ultrasound waves in particular desired shapes and patterns without requiring the complexity and cost of an electronically steered transducer. The transducer may also be an electronically focused device, such as a 2D array or a phased array transducer.

Figure 6A:
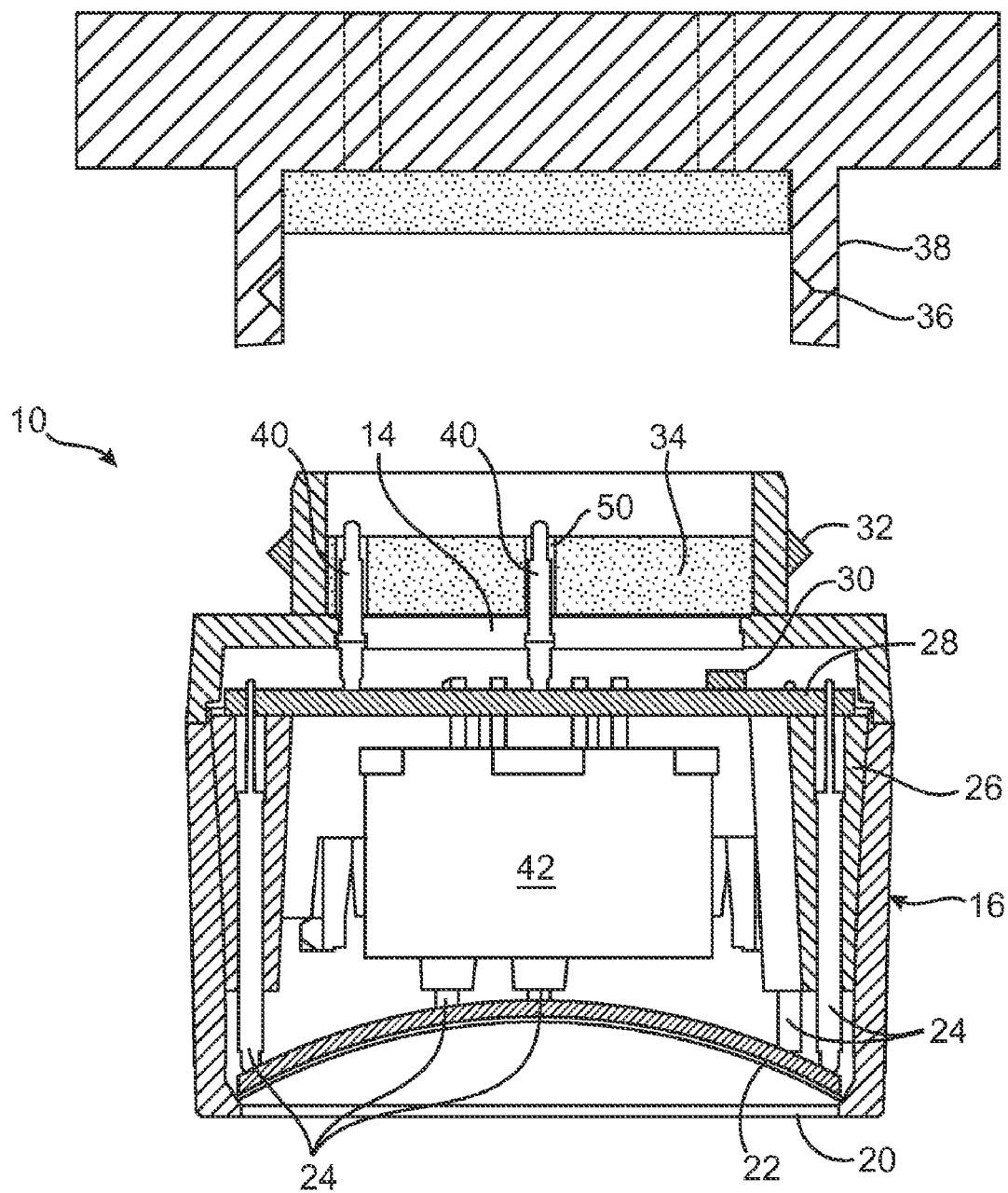
FIGS. 6A-6C show the interchangeable transducer connection to the system socket.

Internal details of the transducer-socket connection are now described (FIG. 6A). In one embodiment, there is a housing 16 having a substantially cylindrical shape. The housing 16 has a neck down region located near the isolation layer 34, and a larger diameter near the transducer 22. The transducer side 20 is open, or has a window so ultrasound energy may be broadcast out of the housing 16 unimpeded. The transducer 22 is secured near the open end 20, and connects to an interface 28 via a set of connection pins 24. The connection pins 24 are held in place with a concentric liner 26 inside the housing 16. The interface 28 may be a set of connecting wires as previously described, or may include a circuit, PCB, PC(B)A or other hardware component. The interface may also have additional electronics, such as a transformer 42 for tuning the transducer 22, a data chip or integrated circuit (IC) 30 to help identify the interchangeable transducer 10 to the medical system 300. Additional components are described below.

Opposite the transducer 22, there is a seal 14 for preventing water or atmosphere from entering the internal compartment of the transducer 10. Working in conjunction with the seal 14 is an isolation layer 34 for reducing pin corrosion and/or cross talk between the external electrical connectors 40. Note the transducer side 20 is also sealed against the outside environment. While the transducer side 20 may be sealed with the transducer 22 itself and various compounds which can be used to prevent leakage, the seal 14 has one or more apertures 50 for the protrusion of the external electrical connectors 40. The apertures 50 are desirably large enough to allow the passage of the electrical connectors 40. The apertures may rely on an interference fit to prevent seepage of fluid between the apertures and the pins, or the use of a sealing agent, or both. The apertures 50 may be sealed once the external electrical connectors 40 are placed using solder, epoxy, resin, adhesive or other suitable sealing agents. A connector 32 is located on the housing and designed for engagement of a corresponding connection on the medical system socket 38. The receiving element 36 and connector 32 form a transducer-system connection. This connection is desirably one having high endurance. Repetitive reliability is desirable, but not required for the transducer connector 32, as it is not envisioned that any one particular transducer will be removed and inserted a large number of times.

The design of the transducer connector 32 and the system side connection (receptor) 36 allow for individual transducers to be interchanged with the medical system 300 on demand. This allows a single medical system to have a great deal of variety in its operational scope. Each new transducer can provide added capability as well as replacement for worn or out dated parts. Desirably the mating of the transducer 10 to the system 300 can be accomplished with a low insertion force connector 32 and receptor 36 combination. Though the insertion force is low, the connection is robust so the transducer 10 will be stable while mounted in socket 38. The socket 38 is desirably connected to a motor assembly through a set of cams 326. Electrical communication between the system 300 and the transducer 10 is maintained regardless of how the socket 38 might be moved.

Figure 6B:
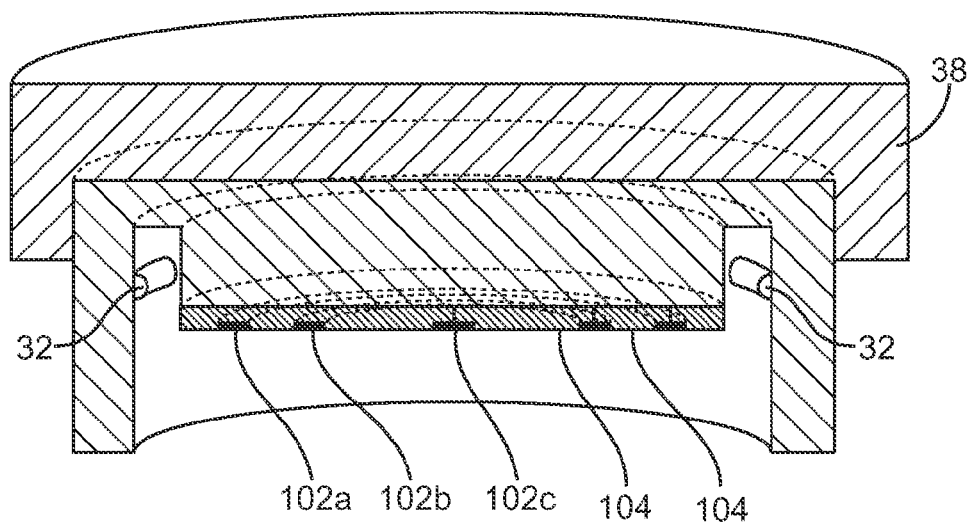
Figure 6B:
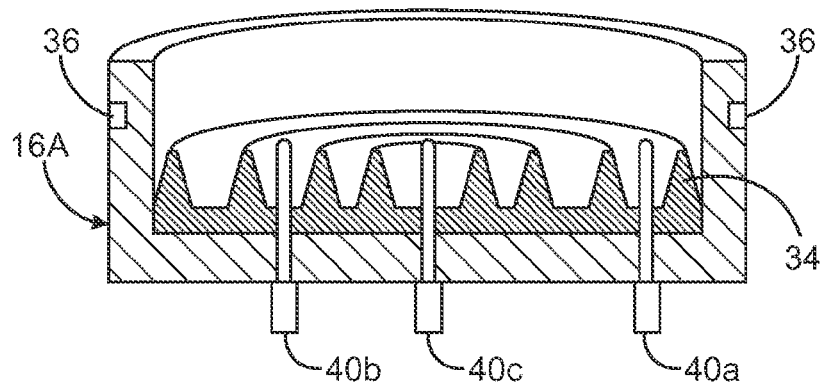
Figure 6C:
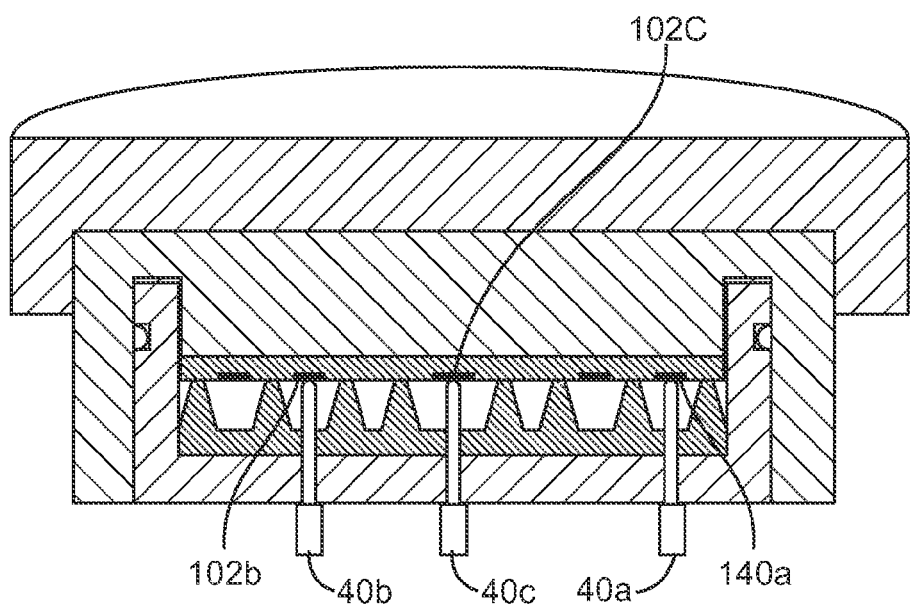

The electrical pin 40 layout as they extend through the seal 34 are designed to make contact with additional lands built into the socket 38 (FIG. 6B). The socket lands 102a-c form concentric structures within the socket. There are isolation rings 104 between the electrical connection lands. The electrical pins 40, now identified individually 40a, 40b, 40c (FIG. 6B) each carry a separate electrical signal from the medical system 100 to the interchangeable transducer 10. The individual connectors may carry power, transmit/receiver signal information, IC chip detection, ground or other signals as desired. The corresponding lands in the socket PCB form concentric rings for connection with each pin separately. This is achieved by arranging the electrical pins 40a-d at a discrete radius from the center of the transducer connector end. Then the transducer housing engages the socket, the pins of the transducer housing match up to the appropriate concentric lands of the slip ring. In this fashion, even if the transducer is rotated within the socket, the proper electrical pin 40a-c always remains in contact with the corresponding land ring forming corresponding pin-land connections 102a-40a, 102b-40b, 102c-40c. There is no limit to the lands 102x and connector pins 40x and as many pairings as are desired may be incorporated into the design. When the transducer is mated with the system, the electrical pins and PCB lands match up, and provide a secure electrical connection (FIG. 6C). The pressure used to hold the removable transducer 10 in place with the system side socket 38 desirably provides sufficient force exerted on the isolation layer 34 to prevent fluid from seeping into the region between the isolation layer 34 and the recess of the housing 16A where the isolation layer is placed. The isolation layer may also be manufactured with flanges on the bottom (not shown) so that isolation layer forms discrete channels or chambers for each electrical connector, or groups of connectors, as the flange or ridge configuration on the top side of the isolation layer.

The pin layout and slip ring described herein and shown in the figures represents one embodiment, however this embodiment is not meant to be limiting of the connector layout. The number of electrical pins in the "plug" end of the transducer may be as many as desired or needed to perform the necessary tasks of providing electrical connection, or even stabilizing plugs for structural integrity. The lands of the slip ring likewise may be as many as desired and it does not necessarily follow that each land will have a corresponding electrical connector. A land may be used as a cross-talk sensor by having no physical pin designed to make contact with it, yet still monitor electrical signal when the connection is made. The land itself can be used as an electrical sensor to monitor the safety and stability of the electrical connection and/or the isolation between lands.

Figure 6D:
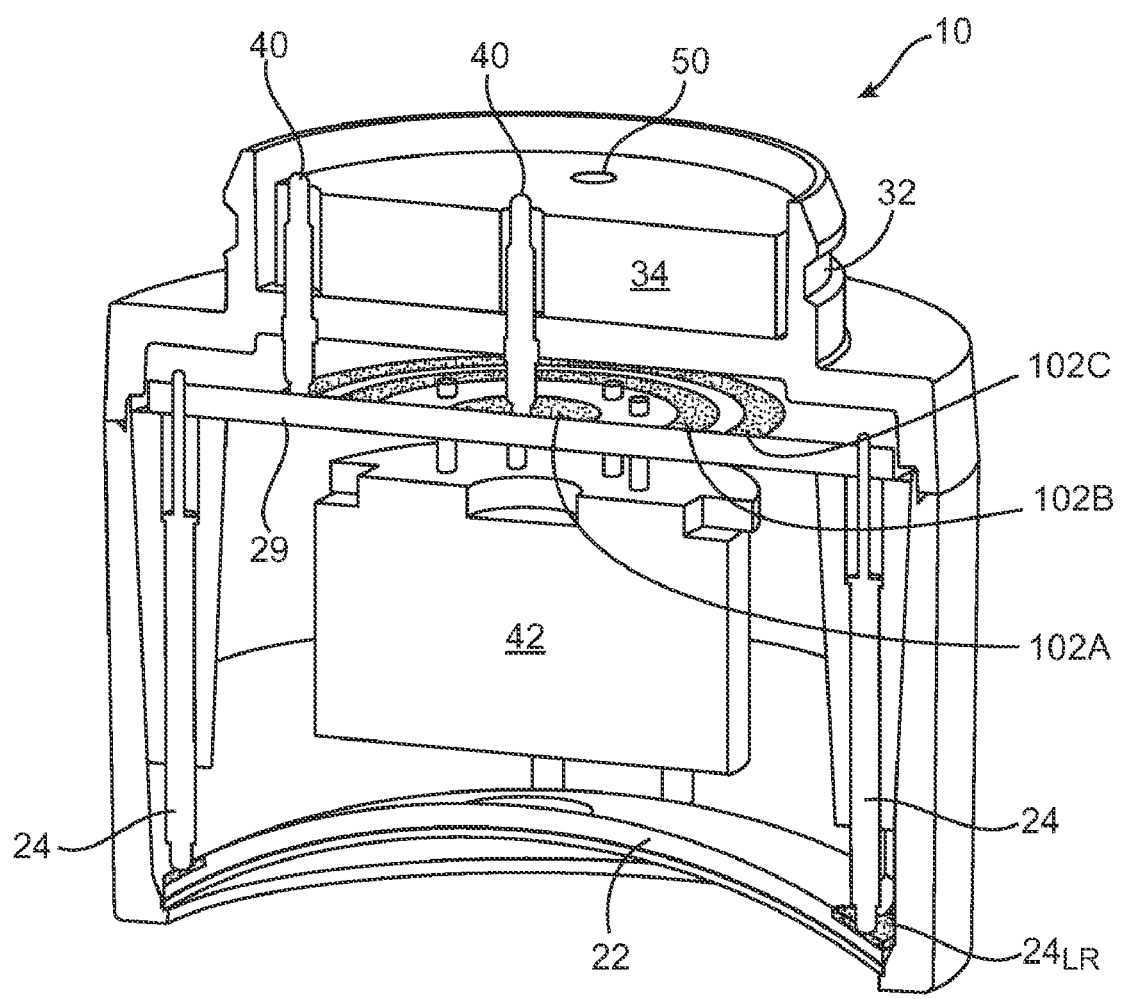
FIGS. 6D-6E show the transducer insert using an alternative PCB.

An alternative embodiment using the pancake slip ring PCB 29 in the insert is now described The transducer insert resembles the assembly previously described. Individual components such as a transformer 42 are still directly connected to the modified PCB 29 (FIG. 6D). The electrical pins 24, 40 are no longer connected to discrete traces on the PCB 29. The electrical pins 24, 40 are now pressed against the trace rings 102a-c on the PCB 29. This allows the top section 16A and bottom section 16B to be press fit together without regard to the orientation of the parts relative to each other. No matter what orientation the top 16A has to the bottom 16B, the electrical pins 24, 40 will still match up with the traces to provide proper electrical communication from the communication port to the transducer.

In another embodiment using either the standard PCB 28 or the slip ring PCB 29, the transducer 22 may have a trace ring 24LR around the circumference of the transducer so the transducer may also be assembled to the bottom 16B section without concern for orientation and placement of the electrical pins 24 to the transducer 22.

Figure 6E:
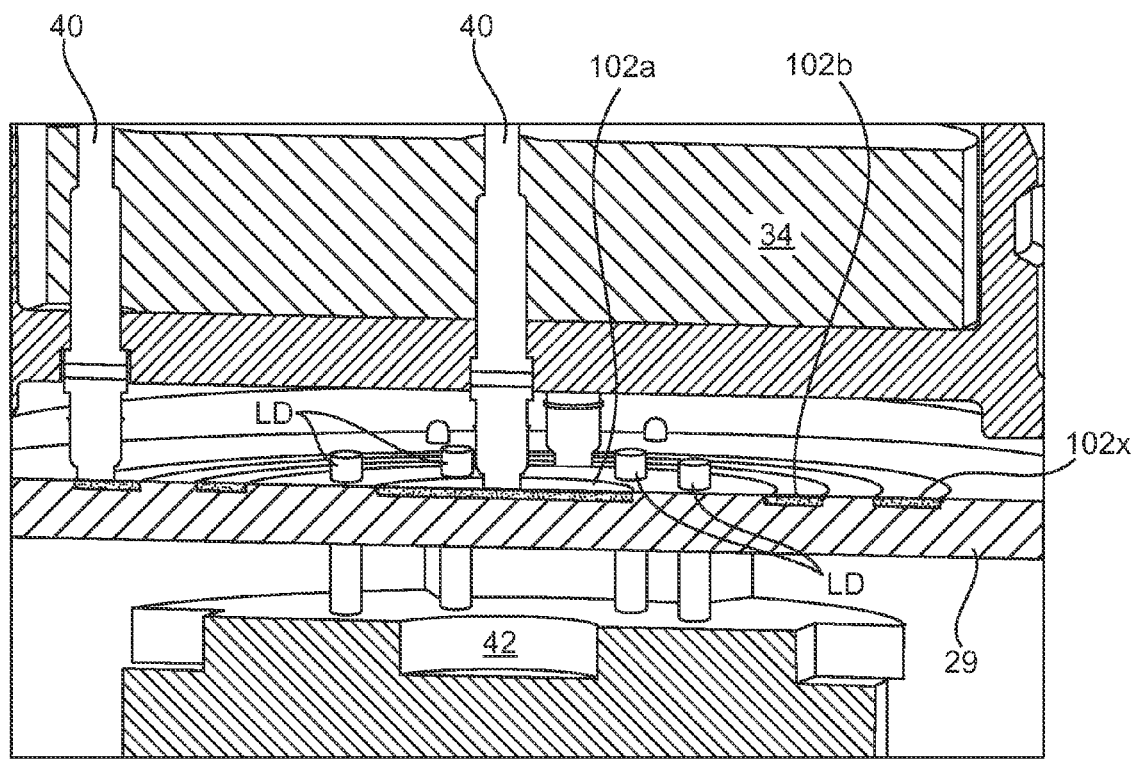
Figure 6F:
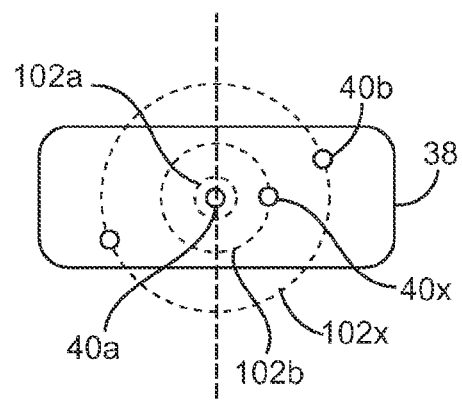
FIGS. 6F-6I illustrate a progression of possible adaptor shapes.

A close up of the electrical pin connections 40 to the top of the slip ring PCB 29 is now shown (FIG. 6E). Here the discrete connections for the transformer 42 are shown in the form of a series of discrete lands LD or trace positions.

Figure 6G:
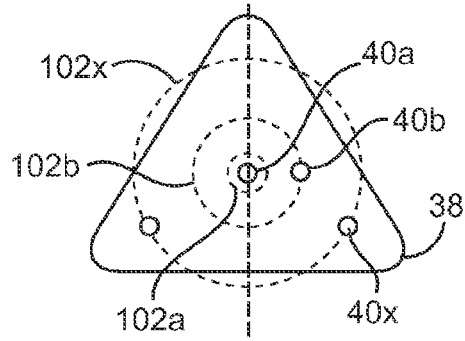
Figure 6H:
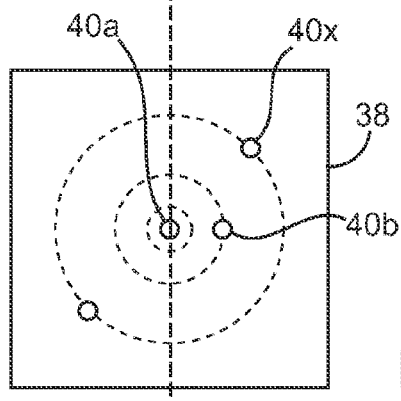
Figure 6I:
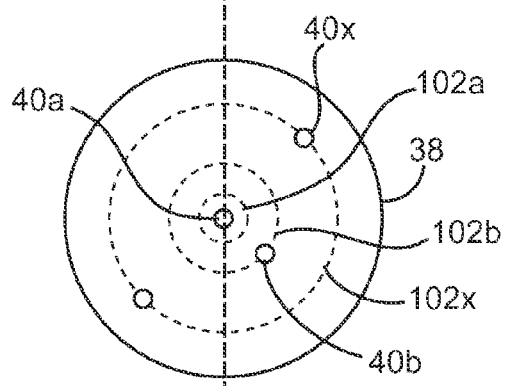

The adaptor for the transducer insert 10 need not be circular, though the circular design is desirable. Various other shapes allowing for multiple orientation of the transducer insert are shown in FIGS. 6G-6I. To simplify the process of replacing the transducer insert 10 for a user, the transducer adaptor has a "keyless" orientation to the "socket" on the system side. So the adaptor may be oblong for two orientations, triangular for three orientations, progressing to a circular insert and socket (FIG. 6I). There is also no restriction on the shape of the adaptor as being a regular shape, so long as the adaptor shape is symmetrical about one axis so the adaptor can still mate with the ultrasound system when it is oriented in another symmetric alignment. Regardless of the physical shape of the insert connector and socket, the socket has electrical contacts in the form of slip rings (dotted lines in FIGS. 6F-6I), with electrical contact pins set at the desired radius to make physical contact with the corresponding land so the appropriate pins 40a-x communicates with the corresponding lands 102a-x.

Figure 7:
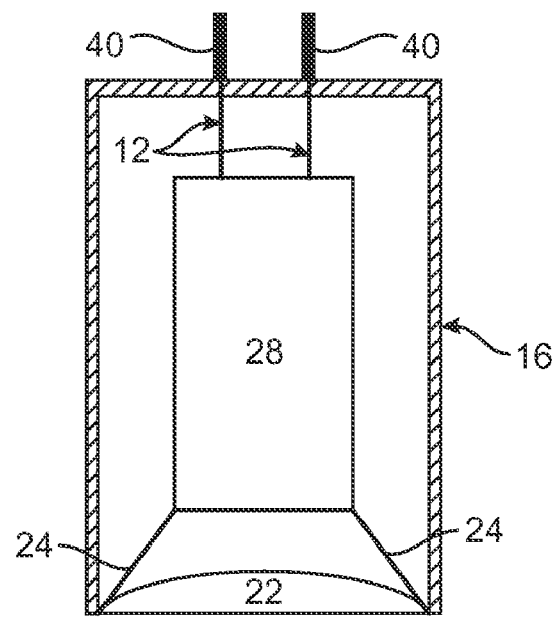
FIGS. 7 and 8 show alternative PCB positions for the interchangeable transducer.

The orientation of the interface 28 as shown in FIGS. 5, 6A-6C need not be perpendicular to the axis of the transducer housing. The interface 28, along with any additional components may be at any orientation desired. In one embodiment, the interface 28 is a PCB or PCA aligned with the axis of the housing 16 (FIG. 7) and has connection wires 12 from the external electronic connectors 40 to a PCB style interface 28 having a transformer 42 and a data IC 30 along with other electronics as may be desired.

Figure 8:
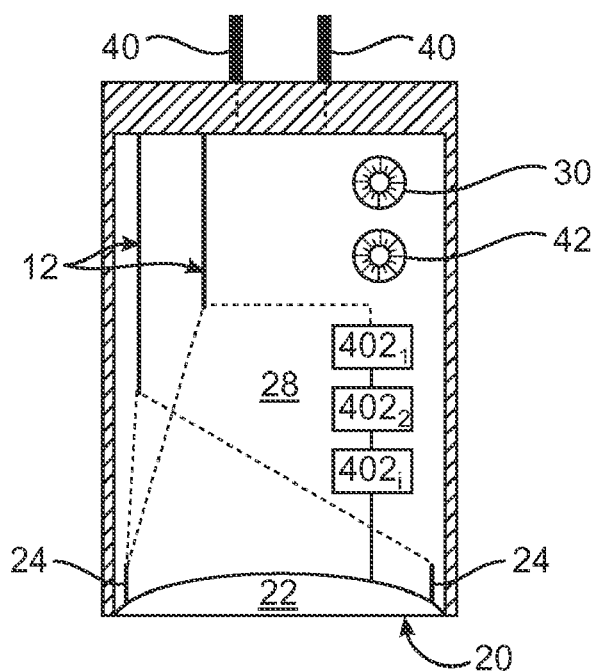

In another embodiment, the interface may be a PCB with a data IC having additional embedded information. The data IC 30 may include data related to the number of uses the transducer is allowed to be activated, or it may record use data which can be used to help improve future interchangeable transducer designs (such as measuring attenuation, feedback, decoupling, thermal information or the like). While this collected data may be stored in the data IC, additional sensors 4021-$i$ could be added to the interface 28 to record the desired data (FIG. 8).

The isolation layer 34 used with the interchangeable transducer may be a washer or disk of electrical isolation material. While the isolation layer may be a solid or otherwise uniform component, an independently novel design for an electrical isolation layer is desirable.

An isolation layer well suited for providing isolation between individual contacts in a wet environment is realized in the form of a slip ring seal (spacer). The slip ring spacer is provided at the docking end of the connectorized transducer. The slip ring spacer may have any one of a variety of forms consistent with the general description and requirements described herein, or similar or equivalent to any of the enumerated embodiments described. The slip ring spacer provides a bumper between the connectorized transducer and the socket of the medical system. Furthermore, the seal provides apertures or other means of allowing electrical communication through the seal, between the connectorized transducer and the socket. In addition, the seal allows for simultaneous electrical communication between multiple isolated electrical connectors in a wet environment. The seal provides isolation of each separate electrical connector type, reducing cross talk between different kinds of signal and/or power connectors. The slip ring seal is desirably made from or has properties incorporated into it, that provide water and electrical resistance. If the material is slightly conductive, it is possible for a short to occur between the electrical pins even in the presence of a partial or complete fluid seal.

A slip ring spacer is now described as shown in FIGS. 9A-9E. The slip ring spacer 900 has a base 902 and one or more flanges or ridges 9041-$i$ rising from the base. The ridges or flanges are adapted to press against a slip ring SR and form one or more concentric channels 9061-$i$ so that each electrical connection ring of the slip ring SR is separated from the other electrical connection rings by the ridges 9041-$i$. When the slip ring seal 900 is pressed against a slip ring SR, channels 9061-$i$ are formed by the ridges or flanges of the slip ring. The ridges are pressed against the slip ring SR, forming a seal against fluid flow between the discrete channels 9061-$i$. The slip ring forms one barrier to fluid movement while the slip ring seal forms the sides and bottom of the channels. In this way, electrically conductive fluid is restricted from flowing between the channels, and exposure to the electrical pins is reduced. This minimizes corrosion and cross-talk among and between the electrical pins. The base desirably has apertures for electrical pins or connectors for making contact with the electrical connection rings on the slip ring. In operation, the slip ring spacer 900 allows each connector to communicate with a corresponding slip ring pad without producing cross talk between other channels, even if the environment is wet.

Figure 9A:
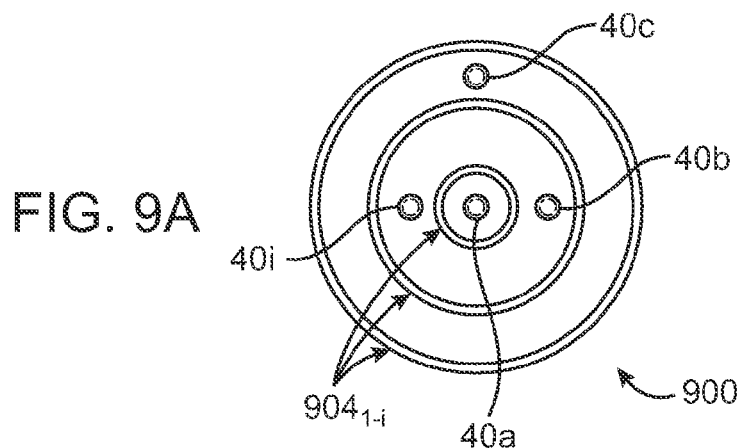
FIGS. 9A-9E show a slip ring seal and a slip ring.
Figure 9B:
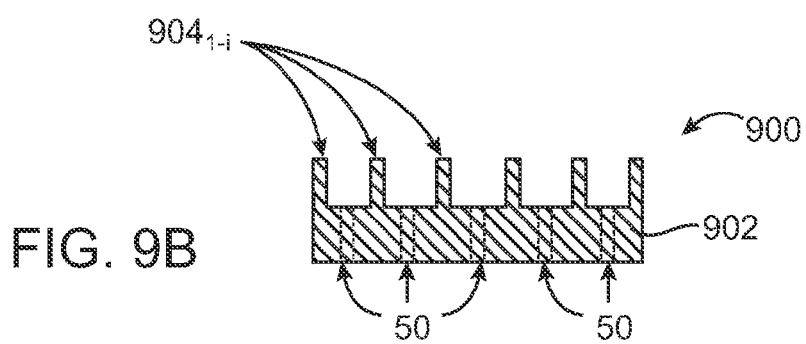
Figure 9E:
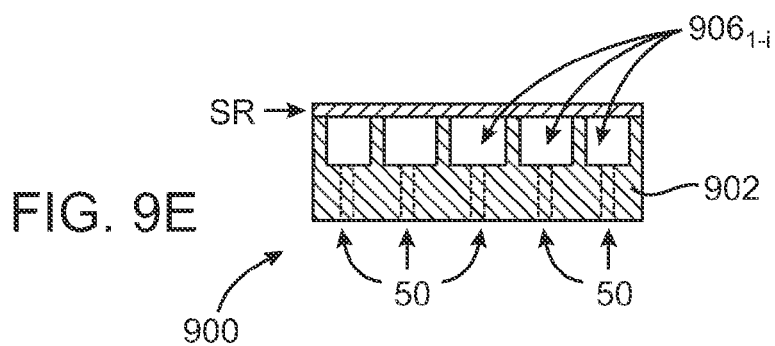
Figure 9C:
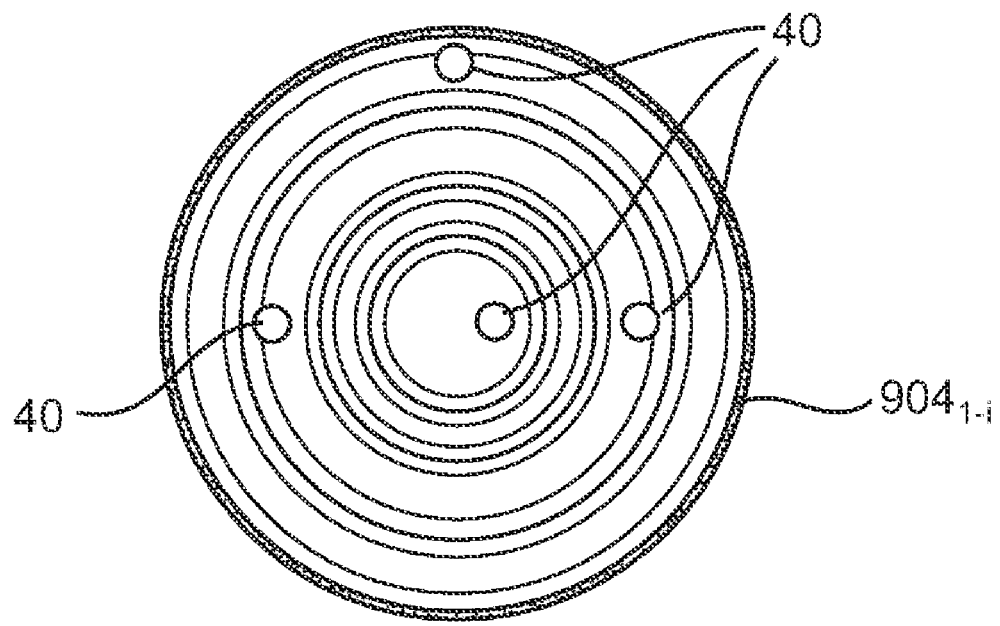
Figure 9D:
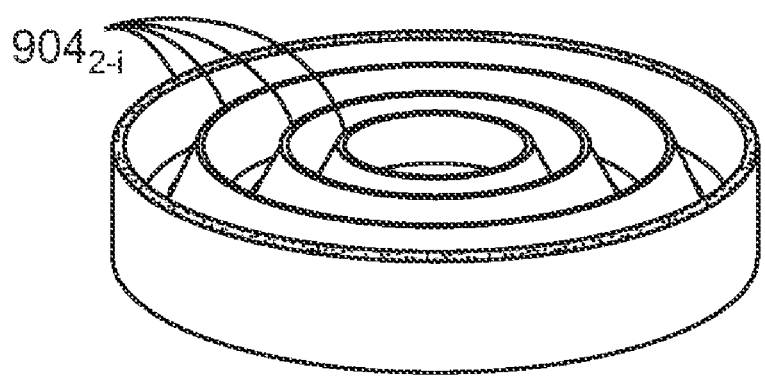

The pin connectors may be organized into groups so that multiple pins may be intended to make contact with a slip ring land. In this case the pins may be organized into groups, similar to the two pins 40$b$, 40$i$ sharing a single circular channel (FIG. 9A). This illustration is an example of more than one pin designed to make contact with a single land, and there is no limit to the number of pins that can be grouped into a single channel or group, or the number of groups that can be used in the interconnection arrangement between the transducer and the socket.

Alternatively the slip ring spacer may have flanges or ridges on the underside of the base (not shown) in a pattern similar to the flange or ridge pattern on the top surface of the spacer. The presence of flanges or ridges on the bottom of the spacer can help isolate the electrical contact pins from one another in the event fluid seeps below the slip ring seal during operation.

Figure 10:
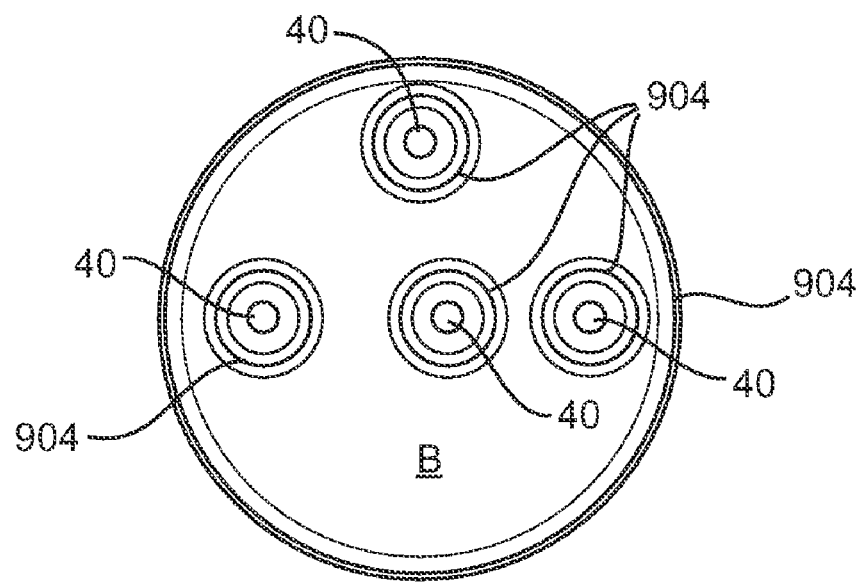
FIGS. 10-15C show alternative embodiments of the slip ring seal.

The slip ring spacer 900 may utilize numerous alternative embodiments. The slip ring spacer 900 has individually isolated electrical pin zones (FIG. 10). In this embodiment each aperture 40 of the slip ring spacer 900 has one or more rising ridges 904 surrounding each aperture. The outer rim of the base 902 is also encircled with a flange or ridge 904R to minimize water or fluid flow from the outside of the connector to the inside components. The individual electrical pins that would protrude through the apertures are individually insulated to reduce the risk of electrode corrosion and/or cross talk.

Figure 11:
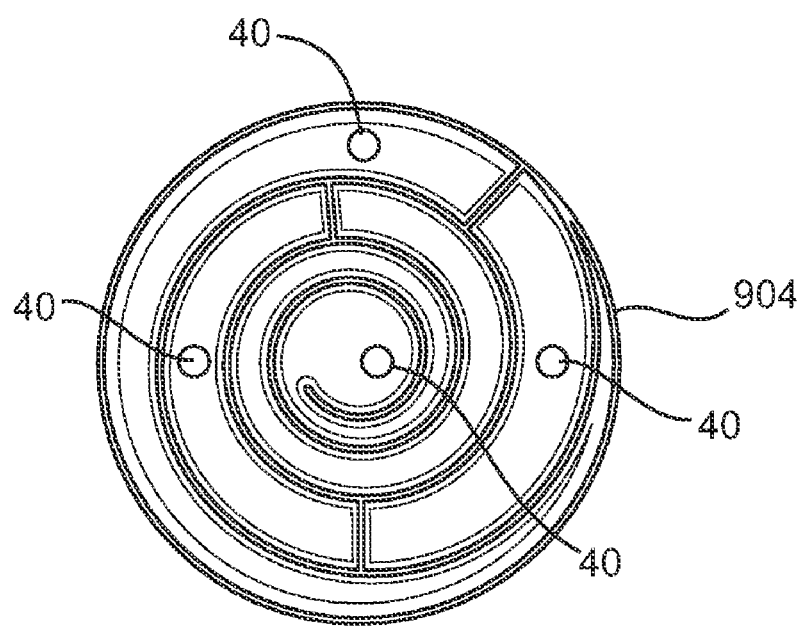
Figure 12A:
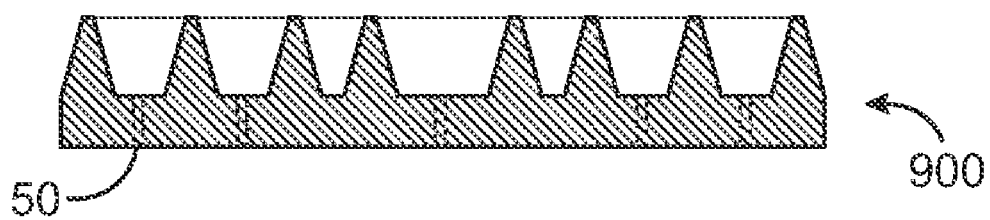
Figure 12B:
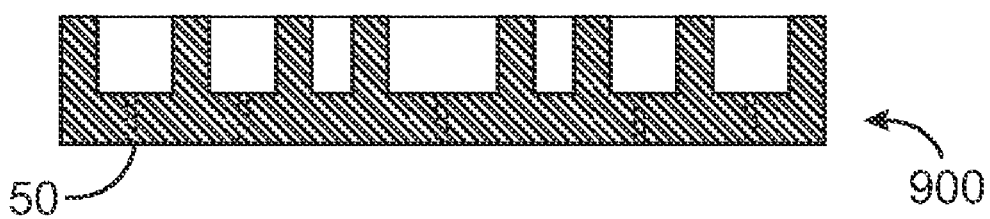
Figure 12C:
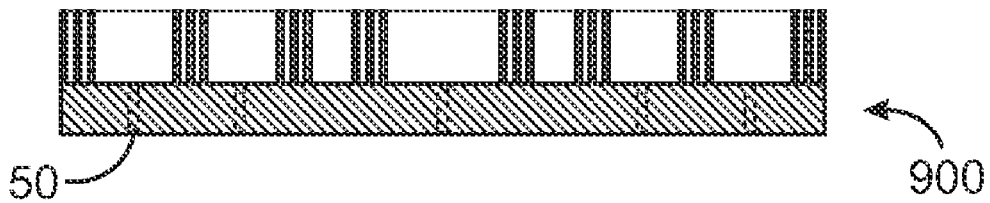

A single spiral channel can be formed with a spiral shaped ridge (FIG. 11) with periodic partitions placed in the spiral pattern. The spacer may use various arrangements of ridges or flanges extending from the base. The ridges may be tapered, block shaped, or arranged in a series of thin partitions operating as a group (FIGS. 12A-12C). Desirably the spacer is made from material that has high water and electrical resistance (like rubber, RTV (Room Temperature Vulcanization) silicone rubber, polymers, etc. . . . ). The material desirably has a durometer low enough to allow the flanges or ridges to deform when they are pressed against a slip ring so the flanges will deform slightly to seal against the slip ring. Designs that are more structurally robust desirably have a lower durometer material with a wider area of contact (FIGS. 12A, 12B) while configurations of the seal having a more rigid construction may use material that is a higher durometer material, but a reduced area of contact (FIG. 12C).

Figure 13A:
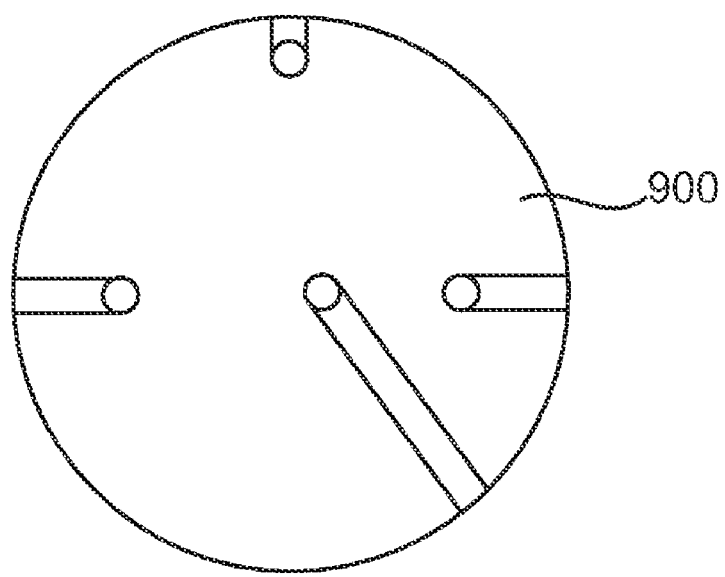
Figure 13B:
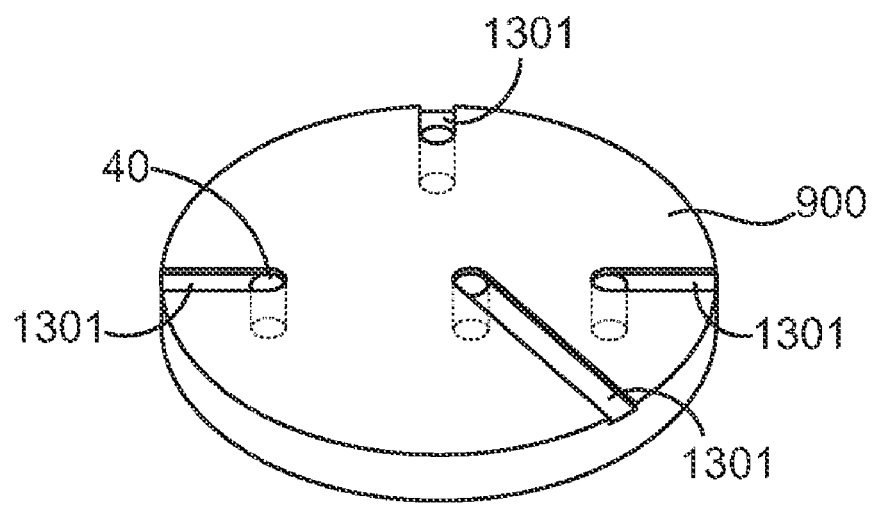

In another embodiment the spacer has a top portion that can compress directly on to the slip ring, and pressure forces any fluid out of the surface area of the slip ring itself so the electrical connection can be made relatively free of any fluid. In another embodiment, temporary channels 1301 may join the apertures for the electrical pins, to the outer circumference of the slip ring seal so water may escape or be forced away from the electrical pin outs (FIGS. 13A-13B). As the seal is pressed against the slip ring, the channels are compressed against the slip ring surface, and thus reducing the flow of fluid among the electrical connections to a level where cross talk between the slip ring lands is acceptable.

Figure 14A:
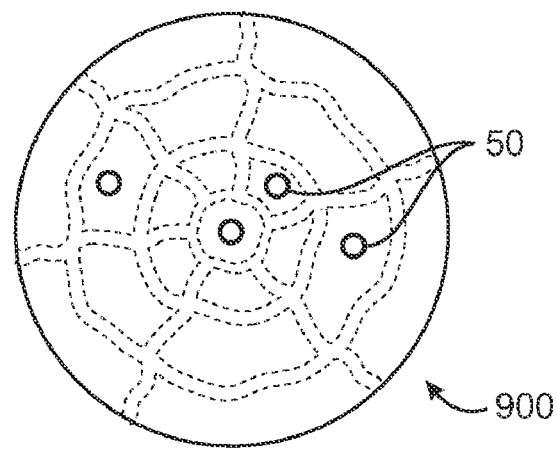
Figure 14B:
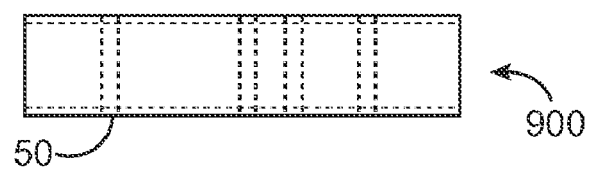
Figure 14C:
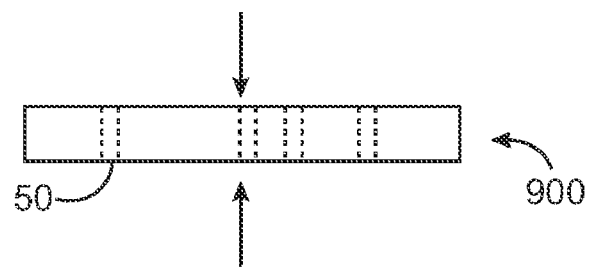
Figure 15A:
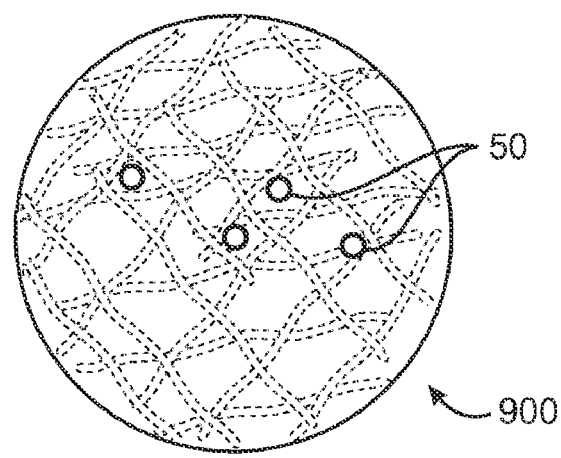
Figure 15B:
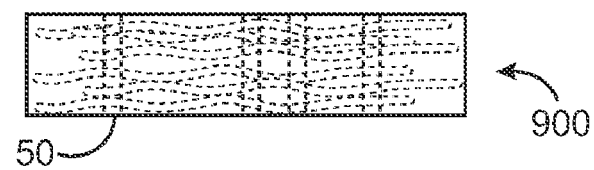
Figure 15C:
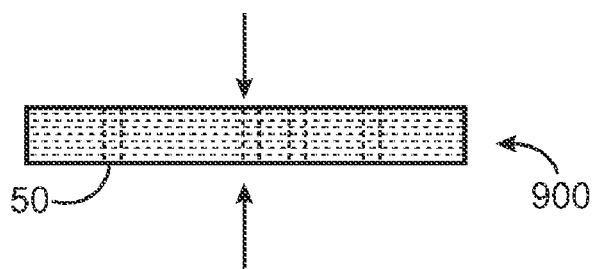

In yet another embodiment of the spacer, the spacer may comprise a water and electrically resistant material having a web like structure (FIG. 14A-14C). Gap spaces between the webbing serve as apertures for the electrical pins to protrude from the transducer and the medical system socket. Optionally the webbing may have additional material between the web strands to further restrict water flow between the web strands when the slip ring seal is compressed into position between the interchangeable transducer and the system socket. As the spacer is pressed against the slip ring while the connectorized transducer is pushed into the socket of the medical system, the webbing with or without additional material in the webbing) collapses and presses fluid out of the cells and away from the electrical connectors. The collapsed webbing forms a barrier to fluid flow between the web strands. The webbing may be organized (FIGS. 14A-14C) or randomly distributed in the formation of the seal (FIGS. 15A-15C).

In operation, a transducer as described herein can be removed from a socket, and then a new one inserted without regard to the radial orientation of the transducer relative to the socket. If the environment containing the socket is wet, the seal on the transducer allows the transducer housing to make good connection on the electrical lands on the socket side, while ensuring solid connection with the transducer and internal workings of the interchangeable transducer. Seams or assembly joints may be sealed with resin or epoxy if needed. Seams and assembly joints may also be sealed with solder, ultrasound welding or similar techniques.

In addition to the embodiments described above, alternative interconnect schemes suitable for use with the present invention are now described. Alternative transducer signal connections include using direct electrical connection via pin and socket, direct electrical connection via soldered spring contact and PCB trace, direct electrical connection via PCB trace to floating spring contact (e.g. in carrier) to PCB trace, direct electrical contact via a post and socket with multiple connections (e.g. stereo headphone jack), as well as wireless types of interconnects, such as inductive coupling, and capacitive coupling.

The transducer can be secured within the housing by gluing it or mechanically affixing it to the housing. The transducer may be sandwiched between a preformed lip in the housing and the electrical connection pins 24. In another embodiment the transducer may be attached using a soluble adhesive allowing for the transducer ceramic to be replaced when the interchangeable transducer fails.

Structurally the physical connector between the transducer housing and the socket may be combined with the electrical connectors. One may visualize a series of stacked electrical connector rings designed to match up to corresponding pin connectors within the socket. Alternatively the relationship of socket and insert may be reversed so the transducer has a socket for receiving a male end adaptor from the medical system.

In other embodiments, the physical connection between the transducer housing and the socket can be achieved through any low force insertion mechanism suitable for the medical system and medical procedures desired. These may include a bearing ring, a snap ring, or simply frictional engagement. Rotational capability of the transducer housing within the socket is not critical, so long as the transducer electronically connects to the medical system electronics through the unaligned electrical connections.

Additional alternative embodiments of the present invention will be readily apparent to those skilled in the art upon review of the present disclosure. The lack of description or the embodiments described herein should not be considered as the sole or only method and apparatus of providing for an interchangeable transducer. The scope of the present invention should not be taken as limited by the present disclosure except as defined in the appended claims.

What is claimed is:

1. An apparatus for use with a medical ultrasound system, the medical ultrasound system including an ultrasonic transducer, the apparatus comprising
a first electrical connector;
a second electrical connector;
a slip ring including a first electrical connection ring and a second electrical connection ring concentrically arranged with the first electrical connection ring, at least one of the first and second electrical connection rings coupled with the transducer; and
a slip ring spacer configured for use with the slip ring, the slip ring spacer comprising a base formed from a non-conductive and fluid resistant material, a first aperture extending through the base, a second aperture extending through the base, a first flange projecting from the base, and a second flange projecting from the base, the first aperture being configured to receive and support the first electrical connector so that a portion of the first electrical connector projects above the first and second flanges to contact the first electrical connection ring, the second aperture being configured to receive and support the second electrical connector so that a portion of the second electrical connector projects above the first and second flanges to contact the second electrical connection ring, the first and second flanges having a concentric arrangement to define a first circular surface region on the base so that the first electrical connection ring of the slip ring is aligned with the first circular surface region.

2. The apparatus spacer of claim 1 wherein the first and second flanges and the first circular surface region form an enclosed space when the slip ring spacer is pressed against the slip ring, the enclosed space being substantially sealed against fluid flow.

3. The apparatus of claim 1 further comprising:
a third flange extending from said base, said third flange having a concentric arrangement with the first and second flanges to define a second circular surface region on the base so that the second electrical connection ring of the slip ring is aligned with the second circular surface region.

4. The apparatus of claim 3 wherein the first and second flanges and the first circular surface region form a first enclosed space and the second and third flanges and the second circular surface region form a second enclosed space when the slip ring spacer is pressed against the slip ring, said first and second enclosed spaces being substantially sealed against fluid flow.

5. The apparatus of claim 3 wherein the second aperture extends through the base within the second circular surface region.

6. The apparatus of claim 3 wherein the second circular surface region is defined between the second and third flanges.

7. The apparatus of claim 1 wherein the non-conductive and fluid resistant material is rubber, RTV (Room Temperature Vulcanization) silicone rubber, or a polymer.

* * * * *

UNITED STATES PATENT AND TRADEMARK OFFICE
CERTIFICATE OF CORRECTION

PATENT NO. : 8,142,200 B2
APPLICATION NO. : 12/051081
DATED : March 27, 2012
INVENTOR(S) : Jeffrey R. Crunkilton et al.

It is certified that error appears in the above-identified patent and that said Letters Patent is hereby corrected as shown below:

In the Specification:

At column 3, line number 63, after "control", delete ",".

At column 6, line number 5, change "Electrical" to --electrical-- and at line number 6, change "Electrical" to --electrical-- and at line number 39, change "requirement,", to --requirement;-- and at line number 57, change "isolated" to --isolate-- and at line number 65, change "used," to --used;--.

At column 7, line number 42, change "visa" to --vice-- and at line number 60, change "are" to --is--.

At column 8, line number 6, change "are" to --is-- and at line number 27, change "allow" to --allows--.

At column 9, line number 64, change "non attached" to --non-attached--.

At column 10, line number 5, change "are" to --is-- and at line number 12, change "or" to --of-- and at line number 22, change "2006." to --2006--.

At column 11, line number 14, change "allow" to --allows--.

Signed and Sealed this
Eighth Day of May, 2012

David J. Kappos
*Director of the United States Patent and Trademark Office*

CERTIFICATE OF CORRECTION (continued)
U.S. Pat. No. 8,142,200 B2

In the Specification:

At column 12, line number 52, change "communicates" to --communicate--.

At column 14, line number 56, after "webbing", insert --(--.